US012208143B2

(12) United States Patent
Walz

(10) Patent No.: US 12,208,143 B2
(45) **Date of Patent: *Jan. 28, 2025**

(54) COMPOSITIONS AND METHODS FOR TRANSPORT ACROSS THE BLOOD BRAIN BARRIER

(71) Applicant: OPHIDION INC., Bethlehem, PA (US)

(72) Inventor: Andreas Walz, Bethlehem, PA (US)

(73) Assignee: OPHIDION INC., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,776

(22) Filed: Jul. 5, 2022

(65) Prior Publication Data

US 2022/0387612 A1 Dec. 8, 2022

Related U.S. Application Data

(60) Continuation of application No. 17/020,613, filed on Sep. 14, 2020, now Pat. No. 11,376,331, which is a continuation of application No. 16/450,831, filed on Jun. 24, 2019, now Pat. No. 10,772,966, which is a continuation of application No. 15/881,300, filed on Jan. 26, 2018, now Pat. No. 10,328,156, which is a division of application No. 15/351,024, filed on Nov. 14, 2016, now Pat. No. 9,913,915, which is a continuation of application No. 14/101,196, filed on Dec. 9, 2013, now Pat. No. 9,522,193, which is a division of application No. 13/487,238, filed on Jun. 3, 2012, now Pat. No. 8,629,114.

(60) Provisional application No. 61/492,884, filed on Jun. 3, 2011.

(51) Int. Cl.

| | |
|---|---|
| ***A61K 47/64*** | (2017.01) |
| ***A61K 31/7088*** | (2006.01) |
| ***A61K 31/713*** | (2006.01) |
| ***A61K 45/06*** | (2006.01) |
| ***A61K 47/42*** | (2017.01) |
| ***A61K 47/56*** | (2017.01) |
| ***C07K 7/08*** | (2006.01) |
| ***C07K 14/00*** | (2006.01) |
| ***C07K 14/47*** | (2006.01) |
| ***C12N 15/113*** | (2010.01) |
| *A61K 48/00* | (2006.01) |

(52) U.S. Cl.

CPC .......... *A61K 47/64* (2017.08); *A61K 31/7088* (2013.01); *A61K 31/713* (2013.01); *A61K 45/06* (2013.01); *A61K 47/42* (2013.01); *A61K 47/56* (2017.08); *C07K 7/08* (2013.01); *C07K 14/00* (2013.01); *C07K 14/4703* (2013.01); *C12N 15/113* (2013.01); *A61K 48/00* (2013.01); *C12N 2310/14* (2013.01); *C12N 2310/3513* (2013.01); *C12N 2320/32* (2013.01)

(58) Field of Classification Search

CPC .. A61K 47/64; A61K 31/7088; A61K 31/713; A61K 45/06; A61K 47/42; A61K 47/56; A61K 48/00; C07K 7/08; C07K 14/00; C07K 14/4703; C12N 15/113; C12N 2310/14; C12N 2310/3513; C12N 2320/32; A61P 25/00; A61P 25/28

See application file for complete search history.

(56) References Cited

U.S. PATENT DOCUMENTS

| | | | |
|---|---|---|---|
| 6,342,581 | B1 | 1/2002 | Rosen et al. |
| 7,135,454 | B2 | 11/2006 | Chimienti et al. |
| 7,691,808 | B2 | 4/2010 | Chimienti et al. |
| 7,875,431 | B2 | 1/2011 | Diehl et al. |
| 2002/0025313 | A1 | 2/2002 | Micklus et al. |
| 2004/0058326 | A1 | 3/2004 | Brooksbank et al. |
| 2004/0110939 | A1 | 6/2004 | Dumas Milne Edwards et al. |
| 2006/0057614 | A1 | 3/2006 | Heintz |
| 2007/0232529 | A1 | 10/2007 | Mickle et al. |
| 2008/0221013 | A1 | 9/2008 | Miwa et al. |
| 2009/0111102 | A1 | 4/2009 | Diehl et al. |
| 2009/0131358 | A1 | 5/2009 | Chatterton |
| 2009/0238754 | A1 | 9/2009 | Wegrzyn et al. |
| 2009/0305970 | A1 | 12/2009 | Linial et al. |
| 2009/0311180 | A1 | 12/2009 | Rohlff |
| 2010/0004162 | A1 | 1/2010 | Heintz et al. |
| 2011/0288011 | A1 | 11/2011 | Castaigne et al. |
| 2012/0148495 | A1 | 6/2012 | Hensch |

FOREIGN PATENT DOCUMENTS

| | | | |
|---|---|---|---|
| JP | 2014-518202 | A | 7/2014 |
| JP | 2017-023909 | A | 2/2017 |
| JP | 2017-095517 | A | 6/2017 |
| JP | 2018-191065 | A | 11/2018 |
| JP | 2019-026648 | A | 2/2019 |

(Continued)

OTHER PUBLICATIONS

Uniprot Protein Database, protein Accession D4A6F2 • D4A6F2_RAT, accessed on Apr. 7, 2023.*

(Continued)

*Primary Examiner* — James H Alstrum-Acevedo
*Assistant Examiner* — Erinne R Dabkowski
(74) *Attorney, Agent, or Firm* — FROST BROWN TODD LLP

(57) ABSTRACT

Compositions and methods are provided including a transporter peptide derived from the loop2 domain of the neuronally-derived lynx1 protein which can be conjugated to an effector agent to form a transporter-effector complex for transport of the therapeutic effector agent to a target that is found across the blood brain barrier.

19 Claims, 11 Drawing Sheets

Specification includes a Sequence Listing.

(56) References Cited

FOREIGN PATENT DOCUMENTS

| | | | |
|---|---|---|---|
| JP | 2020-122025 | A | 8/2020 |
| WO | WO 00/17356 | A2 | 3/2000 |
| WO | WO 2008/054544 | A2 | 5/2008 |
| WO | WO 2012/167214 | A1 | 12/2012 |

OTHER PUBLICATIONS

International Search Report and Written Opinion, corresponding to PCT/US2012/040640, dated Oct. 29, 2012, 11 pages.
"Introduction to Pharmaceutical Dosage Forms"; 1985; Chapter 9: Injections, Biological Products, and Sterile Fluids; Chapter 10: Aerosols, Inhalations, and Sprays; Chapter 13: Ear, Nose, and Topical Oral Preparations; Chapter 14: Suppositories and Other Rectal, Vaginal, and Urethral Preparations; 153 pp.
Alvarez-Erviti, Lydia et al.; "Delivery of siRNA to the mouse brain by systemic injection of targeted exosomes"; Nature Biotechnology; Letters; vol. 29; No. 4; Apr. 2011; pp. 341-347.
Bordo, Domenico et al.; "Suggestions for "Safe"; Residue Substitutions in Site-directed Mutagenesis"; J. Mol. Biol.; 1991; 217; pp. 721-729.
Chen, Wei et al.; "Targeted brain delivery of itraconazole via RVG29 anchored nanoparticles"; Journal of Drug Targeting; 2011; 19(3); pp. 228-234.
Clinton, Lani K. et al.; "Synergistic Interactions between Aβ, Tau, and α-Synuclein: Acceleration of Neuropathology and Cognitive Decline"; Neurobiology of Disease; The Journal of Neuroscience; May 26, 2010; 30; 21; pp. 7281-7289.
Cramer, Paige E. et al.; "ApoE-Directed Therapeutics Rapidly Clear β-Amyloid and Reverse Deficits in AD Mouse Models"; Science; vol. 335; Mar. 23, 2012; pp. 1503-1506.
French, Simon et al.; "What is a Conservative Substitution?"; Journal of Molecular Evolution; 1983; 19; pp. 171-175.
Ibanez-Tallon, Ines et al.; "Novel Modulation of Neuronal Nicotinic Acetylcholine Receptors by Association with the Endogenous Prototoxin lynx1"; Neuron; vol. 33; Mar. 14, 2022; pp. 893-903.
Kumar, Priti et al.; "Transvascular delivery of small interfering RNA to the central nervous system"; Nature; vol. 448; Jul. 5, 2007; pp. 39-45.
Liu, Yang et al.; "Brain-targeting gene delivery and cellular internalization mechanisms for modified rabies virus glycoprotein RVG29 nanoparticles"; Biomaterials; 30; 2009; pp. 4195-4202.
Merrifield, R. B.; "Solid Phase Peptide Synthesis. I. The Synthesis of a Tetrapeptide"; Jul. 20, 1963; pp. 2149-2154.
Miwa, Julie M. et al.; "The Prototoxin lynx1 Acts on Nicotinic Acetylcholine Receptors to Balance Neuronal Activity and Survival In Vivo"; Neuron 51; Sep. 7, 2006; pp. 587-600.
Pardridge, William M.; "Brain Drug Targeting and Gene Technologies"; Jpn. J. Pharmacol.; 87; 2001; pp. 97-103.
Patel, Mayur M. et al.; "Getting into the Brain, Approaches to Enhance Brain Drug Delivery"; CNS Drugs; 2009; 23(1); pp. 35-58.
Pulford, Bruce et al.; "Liposome-siRNA-Peptide Complexes Cross the Blood-Brain Barrier and Significantly Decrease $PrP^{C}$ on Neuronal Cells and $PrP^{RES}$ in Infected Cell Cultures"; PLoS One; Jun. 2010; vol. 6; Issue 6; e11085; 13pp.
Reilly, Jr., William J.; "Pharmaceutical Necessities"; Remington: The Cience and Practice of Pharmacy with Facts and Comparisons; Chapter 55; 2006; pp. 1058-1092.
Rohn, Susanne et al.; "RVG peptide as transfection reagent for specific cdk4 gene silencing in vitro and in vivo"; Journal of Drug Targeting; 2012; 20(4); pp. 381-388.
Schwartz, Joseph B.; "Pharmaceutical Preparations and Their Manufacture"; Remington's Pharmaceutical Sciences; 1980 & 1990; Part 8; Chapters 75-92; pp. 1435-1712.
Taylor, William Ramsay; "The Classification of Amino Acid Conservation"; J. theor. Biol.; 1986; 119; pp. 205-218.
Von Heijne, Gunnar; "SIGPEP: a sequence database for secretary signal peptides"; Short notes; Protein Seq Data Anal; 1987; 1; pp. 41-42.
Von Heijne, Gunnar; "Species-specific variation in signal peptide design Implications for protein secretion in foreign hosts"; Federation of European Biochemical Societies; FEBS Letters; Feb. 1989; vol. 244; No. 2; pp. 439-446.
Xiang, Lixin et al.; "Targeted delivery of large fusion protein into hippocampal neurons by systemic administration"; informa healthcare; Journal of Drug Targeting; 2011; 19(8); pp. 632-636.
Zhan, Changyou et al.; "Loop 2 of Ophiophagus hannah Toxin b Binds with Neuronal Nicotinic Acetylcholine Receptors and Enhances Intracranial Drug Deliver"; Molecular Pharmaceutics; vol. 7; No. 6; Oct. 21, 2010; pp. 1940-1947.
Extended European Search Report for corresponding European Patent Application 12793390.1, mailed Apr. 10, 2015, 9pp.
Ibanez-Tallon, Ines et al.; "Tethering Naturally Occurring Neurotechnique Peptide Toxins for Cell-Autonomous Modulation of Ion Channels and Receptors In Vivo"; Neuron; vol. 43; Aug. 5, 2004; pp. 305-311.
Lentz, Thomas L.; "Synthetic Peptides Corresponding to Sequences of Snake Venom Neurotoxins and Rabies Virus Glycoprotein Bind to the Nicotinic Acetylcholine Receptor"; Proteins: Structure, Function, and Genetics 2:298-307; 1987.
UniProt Protein Database, Ly-6/neurotoxin-like protein 1, Protein accession No. G31920, accessed on Jul. 30, 2014, pp. 1-3.
European Partial Search Report issued in corresponding EP Application No. 18157900.4, dated Apr. 19, 2018, 14 pages.
JP Office action issue in corresponding JP Application No. 2017-023909, English Translation, 3 pages, Jan. 16, 2018.
JP Office action dated Nov. 19, 2019, issued in corresponding JP Application No. 2018-191065, with English translation, 5 pages.
Gong, Cheng et al., "Target delivery of a gene into the brain using the RVG29-oligoarginine peptide", Biomaterials, 33:3456-3463 (2012).
Hwang, Do Won et al., "A brain-targeted rabies virus glycoprotein-disulfide linked PEI nanocarrier for delivery of neurogenic microRNA", Biomaterials, 32:4968-4975 (2011)..
Nashmi, R. et al., "Assembly of a4B2Nicotinic Acetylcholine Receptors Assessed with Functional Fluorescently Labeled Subunits: Effects of Localization, Trafficking, and Nicotine-Induced Upregulation in Clonal Mammalian Cells and in Cultured Midbrain Neurons", The Journal of Neuroscience, 23(37):11554-11567 (2003).
European Patent Office action dated Oct. 15, 2019, issued in corresponding EP Application No. 18157900.4, 4 pages.
Review of Current Issues in Pharmaceutical Excipients, Pharmaceutical Technology, Pharmaceutical Technology—May 2, 2007, vol. 31, Issue 5.
Stephen M. Fuchs, Polyarginine as a multifunctional fusion tag, Protein Science (2005), 14:1538-1544. Published by Cold Spring Harbor Laboratory Press.
Japanese Office action issued in corresponding Japanese Application No. 2020-089946, 3 pages May 18, 2021, including English translation, 4 pages.
Notice of Reasons for Rejection for Japanese Patent Application No. 2022-007151, dated Mar. 7, 2023, and English Translation.
Decision of Refusal for Japanese Patent Application No. 2022-007151, dated Nov. 1, 2023, and English Translation.
Decision of Dismissal of Amendment for Japanese Patent Application No. 2022-007151, dated Nov. 1, 2023, and English Translation.

* cited by examiner

FIG. 9

Human
MTPLLTLILVVLMGLPLAQALDCHVCAYNGDNCFNPMRCPAMVAYCMTTRTYYTPTRMKVSKSCVPRCFETVYDGYSKHASTTSCCQYDLCNGTGLATPATLALAPILLATLWGLL Mouse
MTHLLTVFLVALMGLPVAQALECHVCAYNGDNCFKPMRCPAMATYCMTTRTYFTPYRMKVRKSCVPSCFETVYDGYSKHASATSCCQYYLCNGAGFATPVTLALVPALLATFWSLL Macaque
MTPLLTLFLVVLMGLPLAPVQALDCHVCAYNGDNCFNPMRCPAMVAYCMTTRTYYTPTRMKVSKSCVPSCFETVYDGYSKHASTTSCCQYDLCNSASLAIPATLALAPVLLATLWGLL Cow
MTPLLALFLVALVGLPVAQALDCHVCAYNGENCFNPMRCPAMVSYCMTTRTYYTPTRMKVSKSCVPSCFETVYDGYSKHASTTSCCQYDLCNGAGLATPATLALALLLATLWGLF Chimp
MTPLLTLILVVLMGLPLAQALDCHVCAYNGDNCFNPMRCPAMVAYCMTTRTYYTPTRMKVSKSCVPRCFETVYDGYSKHASTTSCCQYDLCNGAGLATPATLALAPILLATLWGLL Squirrel Monkey
MTPLLTLFLVALLGLPLAQALDCHVCAYNGDNCFNPMRCPAMVAYCMTTRTYYTPTRMKVSKSCVPSCFETVYDGYSKHASTTSCCQYDLCNGAGFAAPATLALAPILLATLWGLL Rat
MTHLLTVFLVALMGLPVAQALECHVCAYNGDNCFKPMRCPAMATYCMTTRTYFTPYRMKVRKSCVPSCFETVYDGYSKHASATSCCQYYLCNGAGFATPVTLALVPALLATFWSLL Ferret
AALLTLFLAALVGLPLAQALDCLDCHVCAYNGENCFNPMRCPAMVSYCMTTRTYYTPTRMKVSKSCVTSCFETVYDGYSKHASTTACCQYDLCNSAGLAVPRTLALAPVLLATLWGLL

SEQUENCE LISTING

```
Sequence total quantity: 33
SEQ ID NO: 1            moltype =   length =
SEQUENCE: 1
000

SEQ ID NO: 2            moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 2
MTTRTYFTPY RMKVRK                                                   16

SEQ ID NO: 3            moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 3
MTTRTYYTPT RMKVSK                                                   16

SEQ ID NO: 4            moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 4
MTWCDYFTPS RGKVRKS                                                  17

SEQ ID NO: 5            moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 5
MTTRTYFTPY RGKVRK                                                   16

SEQ ID NO: 6            moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
```

-continued

```
SEQUENCE: 6
MTTRTYATPY RMKVRKS                                              17

SEQ ID NO: 7           moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 7
MTTRTYFTPY AMADRKS                                              17

SEQ ID NO: 8           moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 8
MPENPRPGTP                                                      10

SEQ ID NO: 9           moltype = AA  length = 26
FEATURE                Location/Qualifiers
REGION                 1..26
                       note = Description of Artificial Sequence: Syntheticpeptide
MOD_RES                1
                       note = Met or Thr
MOD_RES                2
                       note = Thr or Ile
MOD_RES                3
                       note = Thr or Trp
MOD_RES                14
                       note = Arg or Cys
MOD_RES                15
                       note = Thr or Asp
MOD_RES                16
                       note = Tyr, Ile or Gly
MOD_RES                17
                       note = Phe or Tyr
MOD_RES                18
                       note = Thr or Cys
MOD_RES                19
                       note = Pro, Asn or Ser
MOD_RES                20
                       note = Tyr, Thr or Ser
MOD_RES                22
                       note = Met or Gly
MOD_RES                24
                       note = Val or Arg
MOD_RES                25
                       note = Arg, Ser, Ala or Ile
MOD_RES                26
                       note = Lys, Ser or Asp
source                 1..26
                       mol_type = protein
                       organism = synthetic construct
SEQUENCE: 9
XXXMPENPRP GTPXXXXXXX RXKXXX                                    26

SEQ ID NO: 10          moltype = AA  length = 27
FEATURE                Location/Qualifiers
REGION                 1..27
                       note = Description of Artificial Sequence: Syntheticpeptide
source                 1..27
                       mol_type = protein
                       organism = synthetic construct
SEQUENCE: 10
MTTMPENPRP GTPRTYFTPY RMKVRKS                                   27

SEQ ID NO: 11          moltype = AA  length = 29
FEATURE                Location/Qualifiers
REGION                 1..29
                       note = Description of Artificial Sequence: Syntheticpeptide
source                 1..29
                       mol_type = protein
                       organism = synthetic construct
SEQUENCE: 11
```

-continued

```
YTIWMPENPR PGTPCDIFTN SRGKRASNG                                     29

SEQ ID NO: 12          moltype = AA  length = 19
FEATURE                Location/Qualifiers
REGION                 1..19
                       note = Description of Artificial Sequence: Syntheticpeptide
source                 1..19
                       mol_type = protein
                       organism = synthetic construct
SEQUENCE: 12
YTIWCDIFTN SRGKRASNG                                                19

SEQ ID NO: 13          moltype =   length =
SEQUENCE: 13
000

SEQ ID NO: 14          moltype =   length =
SEQUENCE: 14
000

SEQ ID NO: 15          moltype = AA  length = 12
FEATURE                Location/Qualifiers
REGION                 1..12
                       note = Description of Artificial Sequence: Syntheticpeptide
MOD_RES                1
                       note = Thr or Trp
MOD_RES                2
                       note = Arg or Cys
MOD_RES                3
                       note = Thr or Asp
MOD_RES                4
                       note = Tyr, Gly or Ile
MOD_RES                5
                       note = Phe or Tyr
MOD_RES                8
                       note = Tyr or Thr
MOD_RES                10
                       note = Met or Gly
source                 1..12
                       mol_type = protein
                       organism = synthetic construct
SEQUENCE: 15
XXXXXTPXRX KV                                                       12

SEQ ID NO: 16          moltype = RNA  length = 19
FEATURE                Location/Qualifiers
misc_feature           1..19
                       note = Description of Artificial Sequence:
                        Syntheticoligonucleotide
source                 1..19
                       mol_type = other RNA
                       organism = synthetic construct
SEQUENCE: 16
gcactgattt gatagaatt                                                19

SEQ ID NO: 17          moltype = RNA  length = 19
FEATURE                Location/Qualifiers
misc_feature           1..19
                       note = Description of Artificial Sequence:
                        Syntheticoligonucleotide
source                 1..19
                       mol_type = other RNA
                       organism = synthetic construct
SEQUENCE: 17
ctttggtgca tggttactt                                                19

SEQ ID NO: 18          moltype = RNA  length = 19
FEATURE                Location/Qualifiers
misc_feature           1..19
                       note = Description of Artificial Sequence:
                        Syntheticoligonucleotide
source                 1..19
                       mol_type = other RNA
                       organism = synthetic construct
SEQUENCE: 18
gcatctggga gaatgttta                                                19

SEQ ID NO: 19          moltype = RNA  length = 19
FEATURE                Location/Qualifiers
```

-continued

```
misc_feature          1..19
                      note = Description of Artificial Sequence:
                       Syntheticoligonucleotide
source                1..19
                      mol_type = other RNA
                      organism = synthetic construct
SEQUENCE: 19
tggttatcta gagttgcaa                                            19

SEQ ID NO: 20         moltype = AA  length = 16
FEATURE               Location/Qualifiers
REGION                1..16
                      note = Description of Artificial Sequence: Syntheticpeptide
source                1..16
                      mol_type = protein
                      organism = synthetic construct
SEQUENCE: 20
VRITDPSSSR KDHSVN                                               16

SEQ ID NO: 21         moltype = AA  length = 14
FEATURE               Location/Qualifiers
REGION                1..14
                      note = Description of Artificial Sequence: Syntheticpeptide
source                1..14
                      mol_type = protein
                      organism = synthetic construct
SEQUENCE: 21
EVMEQSAGIM YRKS                                                 14

SEQ ID NO: 22         moltype = AA  length = 4
FEATURE               Location/Qualifiers
REGION                1..4
                      note = Description of Artificial Sequence: Syntheticpeptide
source                1..4
                      mol_type = protein
                      organism = synthetic construct
SEQUENCE: 22
RMKV                                                            4

SEQ ID NO: 23         moltype = AA  length = 4
FEATURE               Location/Qualifiers
REGION                1..4
                      note = Description of Artificial Sequence: Syntheticpeptide
source                1..4
                      mol_type = protein
                      organism = synthetic construct
SEQUENCE: 23
AMAD                                                            4

SEQ ID NO: 24         moltype = AA  length = 16
FEATURE               Location/Qualifiers
REGION                1..16
                      note = Description of Artificial Sequence: Syntheticpeptide
source                1..16
                      mol_type = protein
                      organism = synthetic construct
SEQUENCE: 24
MTWCDYFTPY RMKVRK                                               16

SEQ ID NO: 25         moltype = AA  length = 4
FEATURE               Location/Qualifiers
REGION                1..4
                      note = Description of Artificial Sequence: Syntheticpeptide
source                1..4
                      mol_type = protein
                      organism = synthetic construct
SEQUENCE: 25
RGKV                                                            4

SEQ ID NO: 26         moltype = AA  length = 116
FEATURE               Location/Qualifiers
source                1..116
                      mol_type = protein
                      organism = Homo sapiens
SEQUENCE: 26
MTPLLTLILV VLMGLPLAQA LDCHVCAYNG DNCFNPMRCP AMVAYCMTTR TYYTPTRMKV  60
SKSCVPRCFE TVYDGYSKHA STTSCCQYDL CNGTGLATPA TLALAPILLA TLWGLL      116

SEQ ID NO: 27         moltype = AA  length = 116
```

-continued

```
FEATURE                Location/Qualifiers
source                 1..116
                       mol_type = protein
                       organism = Mus sp.
SEQUENCE: 27
MTHLLTVFLV ALMGLPVAQA LECHVCAYNG DNCFKPMRCP AMATYCMTTR TYFTPYRMKV  60
RKSCVPSCFE TVYDGYSKHA SATSCCQYYL CNGAGFATPV TLALVPALLA TFWSLL      116

SEQ ID NO: 28          moltype = AA  length = 118
FEATURE                Location/Qualifiers
source                 1..118
                       mol_type = protein
                       organism = Macaca sp.
SEQUENCE: 28
MTPLLTLFLV VLMGLPLAPV QALDCHVCAY NGDNCFNPMR CPAMVAYCMT TRTYYTPTRM  60
KVSKSCVPSC FETVYDGYSK HASTTSCCQY DLCNSASLAI PATLALAPVL LATLWGLL    118

SEQ ID NO: 29          moltype = AA  length = 116
FEATURE                Location/Qualifiers
source                 1..116
                       mol_type = protein
                       organism = Bos sp.
SEQUENCE: 29
MTPLLALFLV ALVGLPVAQA LDCHVCAYNG ENCFNPMRCP AMVSYCMTTR TYYTPTRMKV  60
SKSCVPSCFE TVYDGYSKHA STTSCCQYDL CNGAGLATPA TLALALILLA TLWGLF      116

SEQ ID NO: 30          moltype = AA  length = 116
FEATURE                Location/Qualifiers
source                 1..116
                       mol_type = protein
                       organism = Pan sp.
SEQUENCE: 30
MTPLLTLILV VLMGLPLAQA LDCHVCAYNG DNCFNPMRCP AMVAYCMTTR TYYTPTRMKV  60
SKSCVPRCFE TVYDGYSKHA STTSCCQYDL CNGAGLATPA TLALAPILLA TLWGLL      116

SEQ ID NO: 31          moltype = AA  length = 116
FEATURE                Location/Qualifiers
source                 1..116
                       mol_type = protein
                       organism = Saimiri sp.
SEQUENCE: 31
MTPLLTLFLV ALIGLPLAQA LDCHVCAYNG DNCFNPMRCP AMVAYCMTTR TYYTPTRMKV  60
SKSCVPSCFE TVYDGYSKHA STTSCCQYDL CNGAGFAAPA TLALAPILLA TLWGLL      116

SEQ ID NO: 32          moltype = AA  length = 116
FEATURE                Location/Qualifiers
source                 1..116
                       mol_type = protein
                       organism = Rattus sp.
SEQUENCE: 32
MTHLLTVFLV ALMGLPVAQA LECHVCAYNG DNCFKPMRCP AMATYCMTTR TYFTPYRMKV  60
RKSCVPSCFE TVYDGYSKHA SATSCCQYYL CNGAGFATPV TLALVPALLA TFWSLL      116

SEQ ID NO: 33          moltype = AA  length = 118
FEATURE                Location/Qualifiers
source                 1..118
                       mol_type = protein
                       organism = Mustela sp.
SEQUENCE: 33
AALLTLFLAA LVGLPLAQAL DCLDCHVCAY NGENCFNPMR CPAMVSYCMT TRTYYTPTRM  60
KVSKSCVTSC FETVYDGYSK HASTTACCQY DLCNSAGLAV PRTLALAPVL LATLWGLL    118
```

COMPOSITIONS AND METHODS FOR TRANSPORT ACROSS THE BLOOD BRAIN BARRIER

CROSS-REFERENCE TO RELATED APPLICATION(S)

The present application is a continuation of, and claim priority to and the benefit of U.S. patent application Ser. No. 17/020,613, filed Sep. 14, 2020, which is a continuation of, and claims priority to and the benefit of U.S. patent application Ser. No. 16/450,831, filed Jun. 24, 2019, now U.S. Pat. No. 10,772,966, which is a continuation of and claims priority to and the benefit of U.S. patent application Ser. No. 15/881,300 filed Jan. 26, 2018, now U.S. Pat. No. 10,328, 156, which is a divisional of and claims priority to and the benefit of U.S. application Ser. No. 15/351,024, filed Nov. 14, 2016, now U.S. Pat. No. 9,913,915, which is a continuation of and claims priority to and the benefit of U.S. application Ser. No. 14/101,196, filed Dec. 9, 2013, now U.S. Pat. No. 9,522,193, which is a divisional of and claims priority to and the benefit of U.S. application Ser. No. 13/487,238, filed on Jun. 3, 2012, now U.S. Pat. No. 8,629,114, which claims priority to and the benefit of U.S. Provisional Application Ser. No. 61/492,884 filed on Jun. 3, 2011, the entire contents of all of which are incorporated herein by reference.

STATEMENT REGARDING FEDERALLY SPONSORED RESEARCH OR DEVELOPMENT

This invention was made with government support under 5R43MH094004-01 and 5R43MH094004-02 awarded by the National Institutes of Health. The government has certain rights in the invention.

SEQUENCE LISTING

The instant application contains a Sequence Listing which was submitted in the priority applications in ASCII format via EFS-Web and is hereby incorporated by reference in its entirety. Said ASCII copy, created on Aug. 8, 2012, is named 02776951.txt and is 18,759 bytes in size.

Additionally, in compliance with the final rule on the "Standard for Presentation of Nucleotide and Amino Acid Sequence Listings Using eXtensible Markup Language (XML) in Patent Applications to Implement WIPO Standard ST.26" (Federal Register, vol. 87, no. 98, 30806-30821) and 37 C.F.R. §§ 1.831 through 1.835 pertaining to the same, the instant application also includes the Sequence Listing submitted in XML format (and in compliance with WIPO Standard ST.26) via EFS-Web, and is also hereby incorporated by reference in its entirety. The XML file, created on Jul. 1, 2022, is named 222300.xml and is 48 kilobytes in size.

FIELD

This disclosure is directed to compositions capable of crossing the blood brain barrier and methods of using these compositions for delivering effector agents to targets inside the blood brain barrier.

BACKGROUND

Diminished cognitive abilities are associated with many disease states (e.g., Alzheimer's disease (AD), Parkinson's disease (PD), depression, schizophrenia, and behavioral disorders such as Attention Deficit Hyperactivity Disorder (ADHD)). These disease states have been consistently among the most detrimental to quality of life. In the past decades, the cholinergic system, especially the nicotinic acetylcholine receptors, have been shown to be of critical importance for normal cognition. Yet despite many efforts, no nicotinic acetylcholine receptor-based cognitive enhancement therapy has been brought to market. Indeed, to date, no effective therapy has been developed to alleviate cognitive decline.

While no effective therapy has yet been developed, many therapeutic compounds showing potential to alleviate cognitive decline have been identified. For example, small interfering RNAs (siRNAs) have great promise due to their exquisite specificity and low toxicity and immunogenicity profiles. Yet challenges remain with the delivery of these intracranial therapeutics, which include overcoming stability issues in the extracellular and intracellular environments, and devising a method for in vivo delivery to specific target cells. Recent studies have indicated that a peptide from the rabies virus glycoprotein (RVG29) successfully delivered intact and functional siRNAs across the blood brain barrier (BBB) by binding to the nicotinic acetylcholine receptor. Similarly, loop 2 of Ophiophagus hannah toxin b (KC2S) has been reported to bind neuronal nicotinic acetylcholine receptors (nAChRs) and enhance intracranial drug delivery. However, the use of rabies-derived or toxin-derived peptides poses safety concerns and possible risks irrespective of their ability to cross the BBB. Indeed, the greatest hurdle is safe and efficient intracranial delivery of the therapeutic agent to the relevant target in the brain.

SUMMARY

In some embodiments of the present invention are directed to compositions and methods including lynx1-loop2 derived peptides that are capable of crossing the blood brain barrier. In other embodiments of the present invention, the lynx1-loop2-derived peptide is conjugated to an effector agent for transport to a target that is found inside the blood brain barrier.

In some embodiments of the present invention, a composition includes a peptide having a sequence of SEQ ID NO:1. In some embodiments, the SEQ ID NO:1 peptide has a sequence selected from SEQ ID NOs:2, 3, 4 and 5. In other embodiments, the SEQ ID NO:1 peptide has a sequence of SEQ ID NO:1 further including a peptide of SEQ ID NO:8 inserted between residues 3 and 4.

In some embodiments of the present invention, a composition includes a peptide having a sequence of SEQ ID NO:1, 2, 3, 4, and 5, and an effector agent. In other embodiments, the SEQ ID NO:1 peptide has a sequence of SEQ ID NO:1 further including a peptide of SEQ ID NO:8 inserted between residues 3 and 4.

In some embodiments, the effector agent is selected from siRNA, shRNA, microRNA, double stranded RNA, strand template RNA, oligonucleotides, modified oligonucleotides, aptamers, analogs and combinations of oligonucleotides, aptamers, genes, peptides, proteins, small chemical molecules, large chemical molecules, viral particles, liposomes, endosomes, exosomes, nanoparticles, dendrimers, positron emission tomography (PET) ligands, eukaryotic cells, prokaryotic cells, microspheres, nanogels, and/or bionanocapsules.

In some embodiments, the effector agent is siRNA conjugated to the peptide.

In some embodiments, a composition includes a peptide having a sequence of SEQ ID NO:13, 14, or 15. In other embodiments, a composition having a peptide having a sequence of SEQ ID NO: 13, 14, or 15 also includes an effector agent.

In some embodiments of the present invention, a method of transporting a lynx1-loop2-derived peptide across the blood brain barrier, includes providing a peptide having the sequence of SEQ ID NO: 1 to a target found in the blood brain barrier, wherein the target may be in vivo or in vitro. In other embodiments, the peptide has a sequence of SEQ ID NO: 2, 3, 4, or 5. In still other embodiments, the peptide has a sequence of SEQ ID NO: 1, further including SEQ ID NO:8 inserted between residues 3 and 4.

In some embodiments of the present invention, a method of transporting an effector agent to a target found within the blood brain barrier is provided, the method including conjugating a peptide having the sequence of SEQ ID NO:1 to an effector agent to form a complex, and providing the complex to the target, wherein the target may be in vivo or in vitro.

In other embodiments, the method includes a peptide having a sequence of SEQ ID NOs: 2, 3, 4, 5, or 10.

In some embodiments, the complex is provided to the target in an in vitro cell culture. In other embodiments, the complex is provided to the target in a mouse or human subject.

In some embodiments, the target is a cell or an extracellular molecule. In some embodiments, the cell is selected from neurons, neuronal cells, brain cells, glial cells, astrocytes, neuronal supporting cells, or cells of the central nervous system. In some embodiments, the target cell includes a nicotinic acetylcholine receptor.

In some embodiments, the effector agent is siRNA, shRNA, microRNA, double stranded RNA, strand template RNA, oligonucleotides, modified oligonucleotides, aptamers, analogs and combinations of oligonucleotides, genes, peptides, proteins, small chemical molecules, large chemical molecules, viral particles, liposomes, endosomes, exosomes, nanoparticles, dendrimers, positron emission tomography (PET) ligands, eukaryotic cells, prokaryotic cells, microspheres, nanogels, or bionanocapsules.

In some embodiments, the composition is a pharmaceutical composition.

In some embodiments of the present invention, a method of transporting a lynx1-loop2-derived peptide across the blood brain barrier, includes providing a peptide having the sequence of SEQ ID NO: 13 to a target found in the blood brain barrier, wherein the target may be in vivo or in vitro. In other embodiments, the peptide has a sequence of SEQ ID NO: 14 or 15.

In other embodiments, a method of transporting an effector agent to a target found within the blood brain barrier, the method includes conjugating a peptide having a sequence of SEQ ID NO:13, 14, or 15 to an effector agent to form a complex, and providing the complex to the target, wherein the target may be in vivo or in vitro.

BRIEF DESCRIPTION OF THE DRAWINGS

FIG. 9 is an alignment of full length lynx1 amino acid sequences from human (SEQ ID NO: 26), mouse (SEQ ID NO: 27), macaque (SEQ ID NO: 28), cow (SEQ ID NO: 29), chimp (SEQ ID NO: 30), squirrel monkey (SEQ ID NO: 31), rat (SEQ ID NO: 32), and ferret (SEQ ID NO: 33) (top to bottom, respectively) with loop2 in bold, according to embodiments of the present invention.

DETAILED DESCRIPTION

Figure 1A:
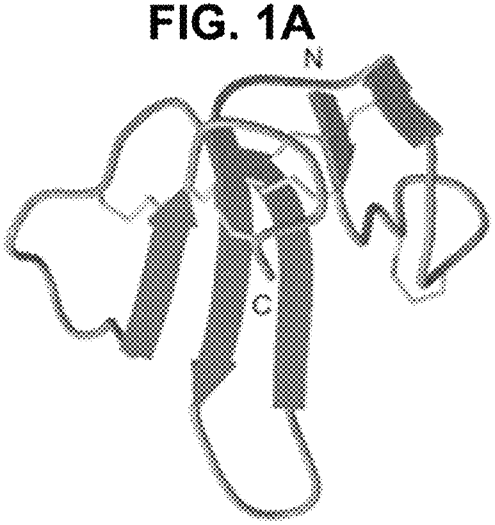
FIG. 1A is a structural depiction of a lynx1 peptide showing the N (amino) and C (carboxy) termini, according to embodiments of the present invention.
Figure 1B:
FIG. 1B is a structural depiction of an α-bungarotoxin protein showing the N (amino) and C (carboxy) termini, according to embodiments of the present invention.
Figure 2:
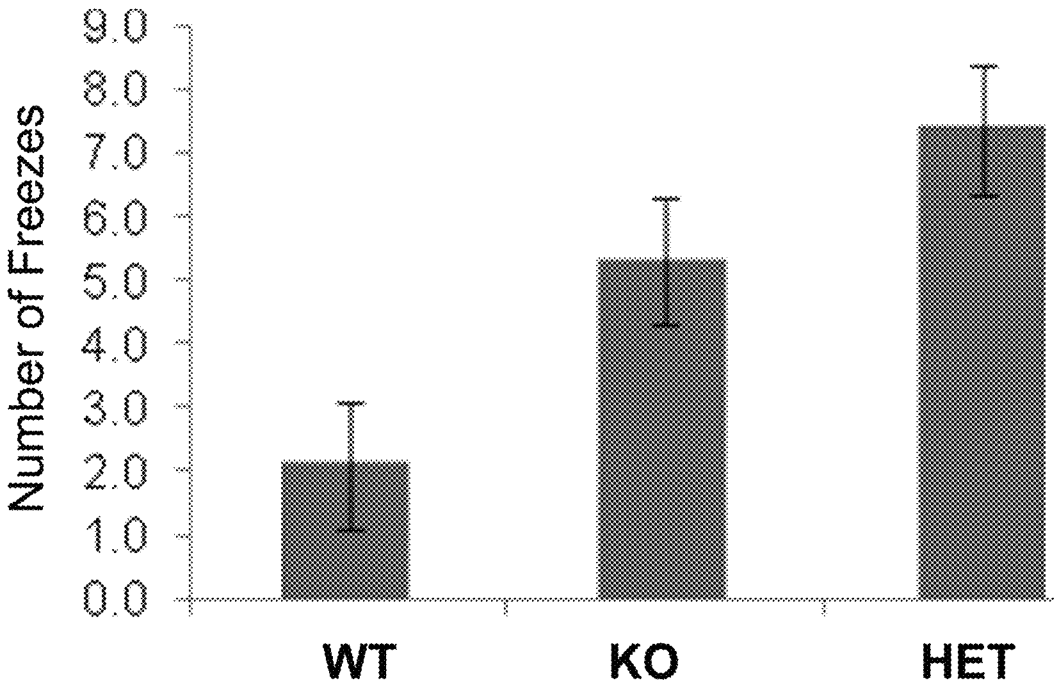
FIG. 2 is a graph showing the number of "freezes" made by wild-type (WT), lynx1 homozygous knockout (KO), and lynx1 heterozygous knockout (HET) mice, according to embodiments of the present invention.

Lynx1 is an accessory molecule to a specific group of neuronal nicotinic acetylcholine receptors, with a striking structural similarity to other nicotinic acetylcholine receptor binding-proteins, such as α-bungarotoxin (FIG. 1), SLURPS, (Secreted Ly-6/uPAR-related proteins), and prostate stem cell antigen. The therapeutic aspects of lynx1 are at least two-fold. First, a decrease in lynx1 function imparts an increase in brain activity. For example, lynx1 knockout mice show significant improvements in an associative learning behavioral assay paradigm (FIG. 2). Second, the lynx1 protein has been shown to bind to neuronal nicotinic receptors (NNRs) or nicotinic acetylcholine receptors (nAChRs), as disclosed in Ibanez-Tallon et al., 2002 *Neuron,* 33:893-903, the entire contents of which are incorporated herein by reference. As disclosed herein, the loop2 region of lynx1 is the putative binding domain for NNRs, and can be used as a peptide transporter for delivery of a therapeutic agent across the blood brain barrier (BBB).

Abbreviations for amino acids are used throughout this disclosure and follow the standard nomenclature known in the art. For example, as would be understood by those or ordinary skill in the art, Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Theonine is Thr or T; Tryptophan is Trp or W; Tyrosine is Tyr or Y; and Valine is Val or V.

In some embodiments of the present invention, a peptide fragment or variant of the second loop (loop2) of lynx1 when conjugated to an effector agent is capable of crossing the blood brain barrier and delivering said effector agents into the brain and/or neurons, as determined by various representative assays and confocal microscopy.

As used herein, a "fragment" of a polynucleotide or polypeptide refers to a smaller set of nucleotides or peptides with respect to the referenced polynucleotide or polypeptide.

As used herein, "variant" of a polynucleotide or polypeptide, refers to a polynucleotide or polypeptide that can vary in primary, secondary, or tertiary structure, as compared to the referenced polynucleotide or polypeptide. For example, a peptide fragment of a lynx1-loop2 peptide is a peptide that may refer to the entire peptide sequence of lynx1-loop2, or a shorter peptide sequence, and this peptide fragment may include amino acid substitutions or deletions as described herein. For example, a "variant" of a lynx1-loop2 peptide, refers to a molecule substantially similar in structure and function to the referenced lynx1-loop2 peptide, but may include additionally moieties or substitutions or changes. As such a variant peptide may include a derivative which is the referenced peptide that has been chemically modified, for example by techniques such as ubiquitination, labeling, pegylation (derivatization with polyethylene glycol) or addition of other molecules. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical.

As used herein, fragments, variants and substantially similar molecules of lynx1-loop2, are collectively referred to as "lynx1-loop2-derived."

As used herein, "effector agent" refers to any molecule that imparts an effect on a target inside the blood brain barrier, and as disclosed herein the target may be target cells or extracellular molecules. Non-limiting examples of effector agents that can be conjugated or linked to lynx1-loop2-derived peptide include: siRNA; short hairpin or stem loop RNA (shRNA); microRNA, double stranded RNA (dsRNA); strand template RNA (stRNA); oligonucleotides (DNA or RNA); modified oligonucleotides (DNA or RNA); aptamers; analogs and combinations of DNA and RNA; genes; peptides including antibody and antigen fragments; proteins, including antibodies and antigens; small chemical molecules; large chemical molecules; viral particles; liposomes; endosomes; exosomes; nanoparticles; dendrimers (e.g. Poly (amidoamine), or PAMAM); positron emission tomography (PET) ligands; eukaryotic cells; prokaryotic cells; microspheres; nanogels; and bionanocapsules.

As used herein, "conjugated," "linked" and "complexed" are used interchangeably. As used herein, the term "conjugated" or "conjugation" refers to the attachment of two or more entities to form one entity. For example, the methods of the present invention provide conjugation of a lynx1-loop2 derived peptide to an effector agent. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each component in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be enzymatically cleavable, acid cleavable, photocleavable, and heat sensitive linkers. Methods for conjugation are well known by persons skilled in the art.

As used herein, "target" refers to a cell or extracellular molecule which is entirely within the BBB-protected central nervous system (CNS) tissue. Extracellular molecules include, but are not limited to extracellular proteins and tissues. An example of extracellular proteins within the BBB, include β-amyloid plaques characteristic of Alzheimer's disease (AD), as disclosed in Cramer et al., *Science,* 335:1503, 2012, the entire contents of which are incorporated herein by reference. In addition to AD, Parkinson's disease and Lewy body dementias are characterized by misfolded protein aggregates called Lewy bodies, and one of the major components of these bodies is the α-synuclein protein, as disclosed in Clinton et al., *J. Neurosci,* 30:7281-7289, 2010, the entire contents of which are incorporated herein by reference.

The term "target cells" as used herein also refers to cells expressing the alpha (α) subunit and/or the beta (β) subunit of the nicotinic acetylcholine receptor. A lynx1-loop2-derived peptide as disclosed herein binds to the alpha-subunit of the nicotinic acetylcholine receptor. Accordingly, a lynx1-loop2-derived peptide as disclosed herein is useful as a targeting moiety for the selective targeting of cells expressing the alpha subunit of the nicotinic acetylcholine receptor. Cells expressing the alpha (α) subunit of the nicotinic acetylcholine receptor include, for example, neurons, glial cells and endothelial cells comprising the blood brain barrier. Target cells of the present invention also include, cells whose endogenous milieu is separated by the BBB, for example, cells in the central nervous system, e.g., brain cells, spinal cord cells, glial cells and other cells supporting neurons, for e.g. astrocytes or "nursing cells" and cells of the central nervous system. In some embodiments, the target cells can be any cell expressing the alpha subunit of the nicotinic acetylcholine receptor or a homologue thereof, such as for example but not limited to neuronal cells in a subject (i.e. in vivo), neuronal cells ex vivo or cultured neuronal cells (i.e. in vitro) such as, for example as primary neuronal cultured cells, or immortalized cell lines expressing alpha and/or beta subunits of the nicotinic acetylcholine receptor either naturally or through stable selection of transfected alpha and/or beta nicotinic acetylcholine receptor constructs. In some embodiments, the target cells are neuronal precursor or neuronal progenitor cells, such as neuronal progenitor stem cells that express an alpha subunit of the nicotinic acetylcholine receptor or a homologue thereof. In some embodiments of the present invention, the target is present within a subject, for example a mammalian subject, for example a human subject. In alternative embodiments, the target is ex vivo, and in further embodiments, the target is in a biological sample, for example in vitro.

Lynx1-Loop2-Derived Peptide

Alignment of the human lynx1-loop2 domain with the lynx1-loop2 sequences from mouse, macaque, cow, chimp, squirrel monkey, rat, and ferret is shown in FIG. 9. In some embodiments of the present invention, a lynx1-loop2-derived peptide confers cellular uptake and/or transport across the BBB, as determined, for example, by cellular imaging or confocal microscopy of brain sections of subjects injected with a lynx1-loop2-derived peptide transporter conjugated to an effector agent, as disclosed herein. Accordingly, in some embodiments of the present invention, a lynx1-loop2-derived peptide is a 16-mer peptide having the general sequence of $X_1$-$X_2$-$X_3$-$X_4$-$X_5$-$X_6$-$X_7$-$X_8$-$X_9$-$X_{10}$-R-$X_{12}$-K-$X_{14}$-$X_{15}$-$X_{16}$, (SEQ ID NO:1) in which for SEQ ID NO:1:

$X_1$ is M or T;
$X_2$ is T or I;
$X_3$ is T or W;
$X_4$ is R or C;
$X_5$ is T or D;
$X_6$ is Y, I, or G;
$X_7$ is F or Y;
$X_8$ is T or C;
$X_9$ is P, N, or S;
$X_{10}$ is Y, T, or S;
$X_{12}$ is M or G;
$X_{14}$ is V or R;
$X_{15}$ is R, S, A, or I; and
$X_{16}$ is K, S, or D.

In some embodiments of the present invention, a lynx1-loop2-derived peptide has a sequence that represents that which is conserved or similar to the aligned sequences found in various species as shown in FIG. 9. For example, a lynx1-loop2-derived peptide that is capable of crossing the BBB includes: MTTRTYFTPYRMKVRK (SEQ ID NO:2), MTTRTYYTPTRMKVSK (SEQ ID NO:3), MTWCDYFTPSRGKVRKS (SEQ ID NO:4), or MTTRTYFTPYRGKVRK (SEQ ID NO:5).

Figure 10:
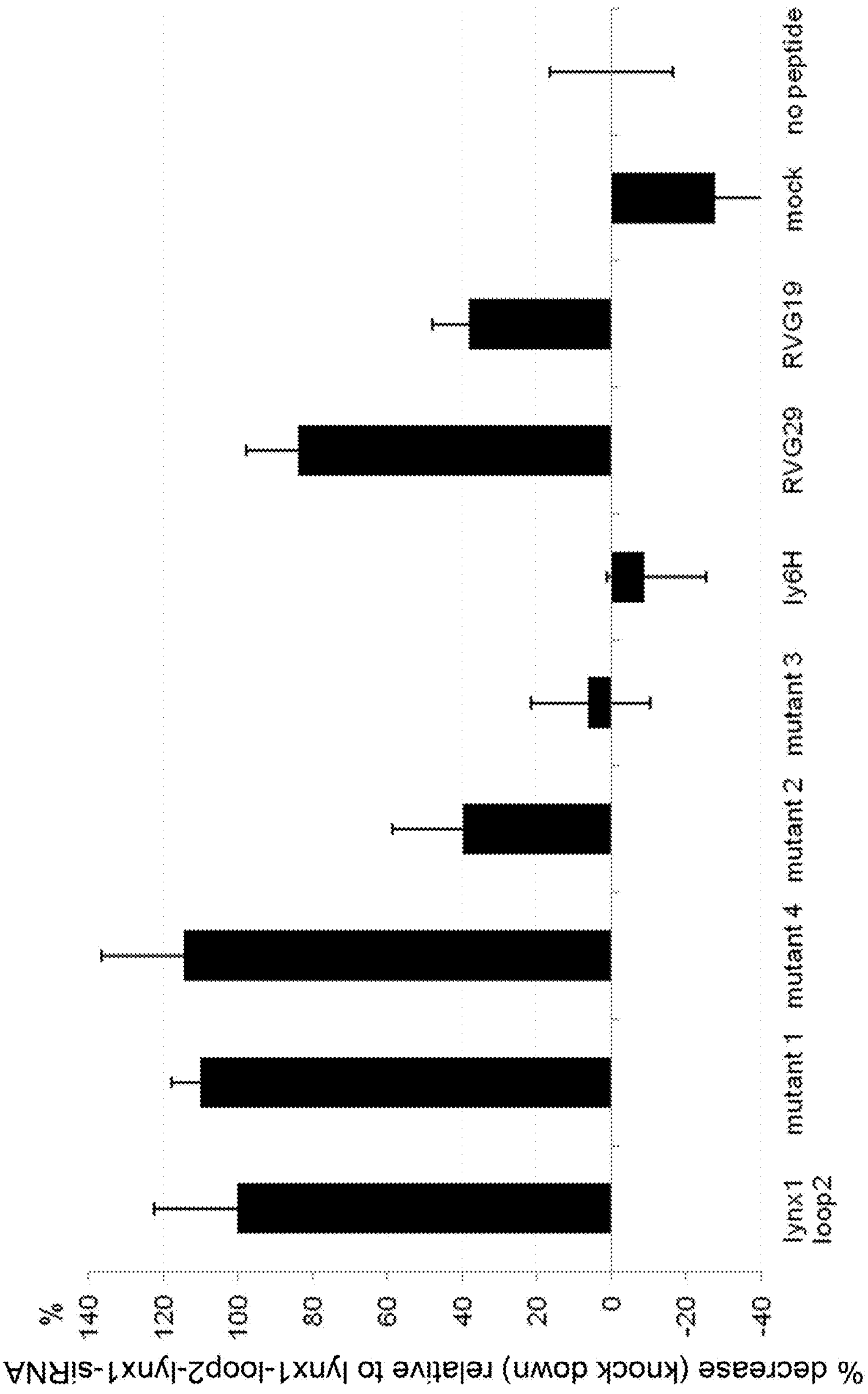
FIG. 10 is a graph showing the effective ability to decrease lynx1 mRNA after delivery of anti-lynx1 siRNA into cultured cortical neurons in which anti-lynx1 siRNA is conjugated to a peptide as indicated (lynx1-loop2, mutant 1, mutant 4, mutant 2, mutant 3, ly6H, RVG29, RVG19, mock (no siRNA) and no peptide (siRNA alone)), where the percent activity to decrease lynx1 mRNA is relative to lynx1 mRNA levels in the presence of lynx1-loop2 anti-lynx1 siRNA (set to 100%), according to embodiments of the present invention.

As shown in FIG. 10, SEQ ID NO:4 (Mutant 1) conjugated to anti-lynx1 siRNA is capable of decreasing lynx1 expression in cultured cortical neurons as well as a peptide having the sequence of SEQ ID NO:2. However, Mutant 2 (MTTRTYATPYRMKVRKS) (SEQ ID NO:6) having the phenylalanine (F) at position 7 substituted with alanine (A), and Mutant 3 (MTTRTYFTPYAMADRKS)(SEQ ID NO:7) having the RMKV (SEQ ID NO: 22) residues at positions 11-14 substituted with AMAD (SEQ ID NO: 23), are not as effective for decreasing lynx1 expression in cultured cortical neurons when conjugated to anti-lynx1 siRNA, as shown in FIG. 10.

In other embodiments of the present invention, additional amino acid sequences may be added to the 16-mer lynx1-loop2 peptide. For example, the sequence of MPENPRPGTP (SEQ ID NO:8) is added to the 16-mer peptide as defined above for SEQ ID NO:1. In one embodiment, MPENPRPGTP (SEQ ID NO: 8) is added between residues $X_3$ and $X_4$ of SEQ ID NO:1 as defined above, to give $X_1X_2X_3$MPENPRPGTP$X_4X_5X_6X_7X_8X_9X_{10}$R$X_{12}$K$X_{14}X_{15}X_{16}$ (SEQ ID NO:9). As shown in FIG. 10, Mutant 4 having a peptide sequence of

MTTMPENPRPGTPRTYFTPYRMK VRKS (SEQ ID NO: 10)

conjugated to an anti-lynx1 siRNA is also capable of decreasing lynx1 mRNA in cultured cortical neurons. SEQ ID NO:8 is a sequence found in RVG29, but is not found in RVG19. RVG 29 has the sequence YTIWMPENPRPGTPCDIFTNSRGKRASNG (SEQ ID NO:11) and RVG19 has the sequence YTIWCDIFTNSRGKRASNG (SEQ ID NO:12). As shown in FIG. 10, lynx1-loop2 (with SEQ ID NO:2 peptide), Mutant 1 (with SEQ ID NO:4 peptide) and Mutant 4 (with SEQ ID NO:10 peptide) all decrease lynx1 mRNA in cultured cortical neurons more effectively than both RVG29 and RVG19 peptides when conjugated to anti-lynx1-siRNA.

In some embodiments, individual substitutions, deletions or additions that alter, add or delete a single amino acid or a small percentage of amino acids may be made to a lynx1-loop2-derived peptide of the present invention. Insertions or deletions are typically in the range of about 1 to 5 amino acids. The choice of conservative amino acids for conservative substitutions may be selected based on the location of the amino acid to be substituted in the peptide, for example if the amino acid is on the exterior of the peptide and exposed to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol. Biol, 1999, 217, 721-739 and Taylor et al, J. Theor. Biol. 119 (1986); 205-218 and S. French and B. Robson, J. Mol. Evol. 19 (1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F; T with S, K, or A; P with A; E with D or Q; N with D or G; R with K; G with N or A; T with S, K, or A; D with N or E, I with L or V, F with Y or L; S with T or A, R with K, G with N or A, K with R; A with S, K, P, G, T, or V; W with Y; and M with L. Considering the results as described herein and shown in FIG. 10 for Mutants 1-4, and in view of the sequences in lynx1 analogs, in some embodiments of the present invention, a lynx1-loop2-derived peptide is a smaller 12-mer peptide having a sequence derived from SEQ ID NO:1 which is $X_3$-$X_4$-$X_5$-$X_6$-$X_7$-$X_8$-$X_9$-$X_{10}$-$R_{11}$-$X_{12}$-$K_{13}$-$X_{14}$ (SEQ ID NO:13) in which for SEQ ID NO:13:

$X_3$ is T or W;
$X_4$ is R or C;
$X_5$ is T or D;
$X_6$ is any amino acid;
$X_7$ is F or Y;
$X_8$ is any amino acid;
$X_9$ is any amino acid;
$X_{10}$ is any amino acid;
$X_{12}$ is M or G; and
$X_{14}$ is V or R.

In an alternative embodiment, a SEQ ID NO:1-derived sequence has the sequence $X_3$-$X_4$-$X_5$-$X_6$-$X_7$-$X_8$-$X_9$-$X_{10}$-R-$X_{12}$-K-$X_{14}$ (SEQ ID NO:14) in which for SEQ ID NO:14:

$X_3$ is T or W;
$X_4$ is R or C;
$X_5$ is T or D;
$X_6$ is Y, G or I;
$X_7$ is F or Y;
$X_8$ is T or C;
$X_9$ is P, N, or S;
$X_{10}$ is Y, T, or S;
$X_{12}$ is M or G; and
$X_{14}$ is V.

In an alternative embodiment, a SEQ ID NO:1-derived sequence has the sequence $X_3$-$X_4$-$X_5$-$X_6$-$X_7$-$X_8$-$X_9$-$X_{10}$-$R_{11}$-$X_{12}$-$K_{13}$-$X_{14}$ (SEQ ID NO:15) in which for SEQ ID NO:15:

$X_3$ is T or W;
$X_4$ is R or C;
$X_5$ is T or D;
$X_6$ is Y, G or I;
$X_7$ is F or Y;
$X_8$ is T;
$X_9$ is P;
$X_{10}$ is Y or T;
$X_{12}$ is M or G; and
$X_{14}$ is V.

All peptides disclosed herein, including lynx1-loop2-derived peptides may be constructed by any appropriate method known in the art. For example, peptides may be synthesized using a peptide synthesizer (Applied Biosystems Model 433) or can be synthesized recombinantly by methods well known in the art. Methods and materials for chemical synthesis of polypeptides are well known in the art. See, e.g., Merrifield, 1963, "Solid Phase Synthesis," J. Am. Chem. Soc. 83:2149-2154. The method by which a peptide of the present invention is synthesized does not limit the present invention. For example, peptides may be commercially purchased from, for example, LifeTein, LLC, or Bio-Synthesis, Inc.

Peptides of the present invention may be modified to accommodate particular target effects. While a lynx1-loop2 peptide may cross the BBB without an effector agent and impart an effect, some desired effects are facilitated with conjugation to an effector agent. As such, peptides may be modified to accommodate specific effector agents. For example, a lynx1-loop2-derived peptide can be modified at the amino terminus, for example, so as to increase hydrophilicity. Increased hydrophilicity enhances exposure of the peptides on the surfaces of lipid-based carriers into which the parent peptide-lipid conjugates have been incorporated for use with liposomes or lipid carriers. Polar groups suitable for attachment to peptides so as to increase their hydrophilicity are well known, and include, for example and without limitation: acetyl ("Ac"), 3-cyclohexylalanyl ("Cha"), acetyl-serine ("Ac Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

Effector Agents

A lynx1-derived peptide of the present invention is capable of crossing the blood brain barrier and is also capable of targeting an effector agent to which it is conjugated for delivery to the target cell and/or molecule. Examples of effector agents and methods by which the effector agents can be conjugated, linked or complexed to a lynx1-derived peptide of the present invention, include: siRNA as disclosed herein and in Kumar et al., *Nature* 448: 39-43, 2007; Pulford et al., PLoS One 5:e11085, 2010; and Rohn et al., *J. Drug Target,* 20: 381-388, 2012, the entire contents of all of which are incorporated herein by reference; hsRNA or microRNA as described in Hwang do et al., *Biomaterials,* 32: 4968-4975, 2011, the entire contents of which are incorporated herein by reference; oligonucleotides (DNA or RNA) as described in Pardridge, *Jpn J. Pharmacol,* 87:97-103, 2001, the entire contents of which are incorporated herein by reference; modified oligonucleotides (e.g., DNA or RNA) as described in Pardridge, 2011, *supra*; genes as described in Pardridge, 2011, *supra*, and Gong et al., *Biomaterials,* 33:3456-3463, 2012, the entire contents of which are incorporated herein by reference; peptides and PET ligands as described in Pardridge, 2011, *supra*; proteins as described in Pardridge, 2011, *supra*, and Xiang et al., *J Drug Target,* 19:632-636, 2011, the entire contents of which are incorporated herein by reference; small chemical molecules as described in Zhan et al., *Mol Pharm,* 7:1940-1947, 2010, the entire contents of which are incorporated herein by reference; large chemical molecules; viral particles; liposomes as described in Pulford et al., 2010, *supra*; endosomes; exosomes as described in Alvarez et al., *Nat. Biotechnol.,* 29:341-345, 2011, the entire contents of which are incorporated herein by reference; nanoparticles as described in Chen et al., *J Drug Target,* 19:228-234, 2011 and Liu et al., *Biomaterials,* 30:4195-4202, 2009, the entire contents of both of which are incorporated herein by reference; dendrimers (e.g. PAMAM) as described in Liu et al., *supra*; eukaryotic cells; prokaryotic cells; and microspheres, nanogels, and bionanocapsules as described in Patel et al., *CNS Drugs,* 23:35-58, 2009, the entire contents of which are incorporated herein by reference.

In some embodiments of the present invention, the effector agent, for example an siRNA therapeutic agent as disclosed herein, can be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions.

In some embodiments, the effector agent of the present invention can be transported to various target cells or tissues. For example, the effector agent of the present invention can be transported to any nerve cell, e.g. nerve cell in the central nervous system, olfactory, or visual system. The effector agent of the present invention can also be transported to a neurologically related target cell or tissue, e.g. cells or tissues that interact with or are targets of the nervous system.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It can contain elements at which regulatory proteins and molecules can bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA.

For the translocation of a gene into the nucleus of a target cell, a signal sequence may be conjugated to the effector agent gene. Many nuclear signal sequences are known in the art. A nuclear membrane signal sequence or peptide is a sequence of amino acids generally of a length of about 10 to about 50 or more amino acid residues, many (typically about 55-60%) residues of which are hydrophobic such that they have a hydrophobic, lipid-soluble portion. Generally, a signal peptide is a peptide capable of penetrating through the cell membrane (e.g. the nuclear membrane) to allow the import and/or export of cellular proteins. Such a signal sequence may be naturally present in the gene or may be provided using many well known recombinant DNA techniques.

Signal peptide sequences can be selected from the SIGPEP database (von Heijne, Protein Sequence Data Analysis 1:4142 (1987); von Heijne and Abrahmsen, L., FEBS Letters 224:439-446 (1989)), the entire contents of both of which are incorporated herein by reference.

Transport Across the Blood Brain Barrier Using Lynx1-Loop2-Derived Peptide

In some embodiments of the present invention, a method of transporting a peptide across the blood brain barrier to a target therein, includes providing a lynx1-loop2-derived peptide to a subject or cell culture containing the target. In some embodiments, a lynx1-loop2-derived peptide that can reach a target found within the BBB has a sequence of SEQ ID NO:1. In other embodiments, the peptide has a sequence of SEQ ID NO: 2, 3, 4 or 5. In still other embodiments, the peptide has a sequence of SEQ ID NO:1 wherein a peptide of SEQ ID NO:8 is inserted between residues 3 and 4.

Transport of an Effector Agent Using a Lynx1-Loop2-Derived Peptide

In some embodiments of the present invention, a method of transporting an effector agent to target cells includes conjugating a lynx1-loop2-derived peptide to an effector agent to form a complex, and providing the complex to the target cells or to a subject having the target cells.

In some embodiments, the method includes a lynx1-loop2 peptide of SEQ ID NO:1. In other embodiments, the method includes a lynx1-loop2-peptide selected from SEQ ID NOs: 13, 14, or 15. In still other embodiments, the method includes a lynx1-loop2-peptide selected from SEQ ID NOs: 2, 3, 4, 5, or 10, in which transport to the target cells is determined by measuring the effect of the conjugated effector agent. In some embodiments, measuring the effect of the conjugated effector agent includes imaging the effector agent at the target. In additional embodiments, measuring the effect of the conjugated effector agent includes assaying the presence of the effector agent, by measuring an increase or decrease in an activity or level of protein or nucleic acid. For example, if the effector agent is siRNA, the levels of the mRNA that correspond to the siRNA can be measured after providing a complex of the siRNA conjugated to a lynx1-loop2-derived peptide, in which an effect is indicative of the effector agent being delivered to the target.

In some embodiments, the method of transporting an effector agent occurs in a target cell selected from brain cells, spinal cord cells, glial cells, neurons, molecules and other cells of the central nervous system. In some embodiments, the method of transporting an effector agent to target cells includes providing the complex to a subject in which the target cells are within the blood brain barrier. In other embodiments, the subject having the target cells is a human. In some embodiments, the method of transporting an effector agent to a target that is found inside the BBB, occurs in vitro.

In some embodiments of the method, the effector agents include siRNA; short hairpin or stem loop RNA (shRNA); microRNA, double stranded RNA (dsRNA); strand template RNA (stRNA); oligonucleotides (DNA or RNA); modified oligonucleotides (DNA or RNA); analogs and combinations of DNA and RNA; aptamers; genes or gene products; peptides including antibody and antigen fragments; proteins, including antibodies and antigens; small chemical molecules; large chemical molecules; viral particles; liposomes; endosomes; exosomes; nanoparticles; dendrimers; positron emission tomography (PET) ligands; eukaryotic cells; prokaryotic cells; microspheres; nanogels; and/or bionanocapsules.

In other embodiments of the method, the effector agent is siRNA. For example, as disclosed herein, the siRNA is a lynx1 siRNA that is conjugated to lynx1-loop2-derived peptide.

In some embodiments of the method, the complex is a pharmaceutical composition.

The terms "composition" or "pharmaceutical composition" are used interchangeably herein and refer to compositions or formulations that usually comprise an excipient, such as a pharmaceutically acceptable carrier that is conventional in the art and that is suitable for administration to mammals, and for example, humans or human cells. Such compositions can be specifically formulated for administration via one or more of a number of routes, including but not limited to, oral, parenteral, intravenous, intraarterial, subcutaneous, intranasal, sublingual, intraspinal, intracerebroventricular, and the like. Cells administered a composition as disclosed herein can be part of a subject, for example for therapeutic, diagnostic, or prophylactic purposes. The cells can also be cultured, for example cells as part of an assay for screening potential pharmaceutical compositions, and the cells can be part of a transgenic animal for research purposes. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, see University of the Sciences in Philadelphia (2005) Remington: The Science and Practice of Pharmacy with Facts and Comparisons, 21st Ed.

Compositions as disclosed herein can be administered by any convenient route, including parenteral, enteral, mucosal, topical, e.g., subcutaneous, intravenous, topical, intramuscular, intraperitoneal, transdermal, rectal, vaginal, intranasal or intraocular. In one embodiment, the compositions as disclosed herein are not topically administered. In one embodiment, the delivery is by oral administration of the composition formulation. In one embodiment, the delivery is by intranasal administration of the composition, especially for use in therapy of the brain and related organs (e.g., meninges and spinal cord). Along these lines, intraocular administration is also possible. In another embodiment, the delivery means is by intravenous (i.v.) administration of the composition, which is especially advantageous when a longer-lasting i.v. formulation is desired. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

The compositions as disclosed herein can be administered in prophylactically or therapeutically effective amounts. The targeted delivery compositions as disclosed herein can be administered along with a pharmaceutically acceptable carrier. A prophylactically or therapeutically effective amount means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

The "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and is compatible with administration to a subject, for example a human. For the clinical use of the methods according to some embodiments of the present invention, targeted delivery compositions according to some embodiments are formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound according to some embodiments of the invention in combination with one or more pharmaceutically acceptable ingredients. The carrier can be in the form of a solid, semi-solid or liquid diluent, cream or a capsule. These pharmaceutical preparations are a further object according to some embodiments of the invention. Usually the amount of active compounds is between 0.1-95% by weight of the preparation, for example, between 0.2-20% by weight in preparations for parenteral use and for example, between 1 and 50% by weight in preparations for oral administration.

The terms "parenteral administration" and "administered parenterally" as used herein refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

As used herein, the terms "administering," "introducing," and "providing" are used interchangeably, and according to embodiments of the present invention, refer to the placement of the pharmaceutical composition including a lynx1-loop2-derived peptide with or without a conjugated effector agent into a subject or in vitro culture by a method or route which results in at least partial localization of the agents at a desired site (e.g. target cells and/or molecules). The agents of the present invention can be administered by any appropriate route which results in an effective treatment in the subject.

In the preparation of pharmaceutical formulations containing the targeted delivery composition of the present invention in the form of dosage units for oral administration the compound selected can be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

The following Examples are presented for illustrative purposes only, and do not limit the scope or content of the present application.

Examples

Example 1. Effect of lynx1 observed in mice. Compelling biological proof-of-principle was demonstrated by manipulating lynx1 in genetically engineered mice. (See Miwa et al., *Neuron,* 51:587-600, 2006, the entire contents of which are incorporated herein by reference.) Lynx1 knockout mice show significant improvements in an associative learning behavioral assay paradigm (FIG. 2). Considering the dampening effects of lynx1 on nicotinic acetylcholine receptors and the fact that low cholinergic tone is associated with reduced cognitive function, this result indicates that removal of lynx1 indeed increases cholinergic tone. Since the same lynx1 knockout mice, however, did show neurodegenerative phenotypes in later stages of their lives, complete removal of lynx1 over extended periods of time appears to shift the cholinergic activity potentially outside the optimal window into the hyperactive end of the spectrum. Bearing this out is the fact that partial reduction of lynx1 in heterozygous lynx1 knockout mice did not show any neurodegeneration at all. Interestingly, cognitive enhancement was even further improved as compared to homozygous lynx1 knockout or wild-type animals (FIG. 2). Thus, a wide range of lynx1 dosages appear to be a viable strategy to fine tune cholinergic tone. It is noteworthy that manipulating nicotinic acetylcholine receptors themselves have not produced comparable results, indicating that lynx1 manipulation may actually prove to be a more desirable way to develop cognitive enhancement drug therapeutics based on nicotinic acetylcholine receptors and may be on par with or superior to other cognitive enhancement strategies.

Specifically, FIG. 2 shows enhanced associative learning ability for lynx1 homozygous knockout (KO) and heterozygous lynx1 knockout (HET) mice compared to wild-type (WT) in fear conditioning assays. Mice were conditioned by the pairing of an innocuous stimulus, a tone, with a noxious stimulus, a mild foot shock, and fear was measured by freezing. The following day, lynx1 KO animals exhibited more freezing to the benign tone than WT animals, indicating better associative learning than WT mice. The HET animals performed even better than KO animals in this task. $P<0.05$ for lynx1KO and HET animals. Y-axis is the number (#) of freezes:

Example 2. qPCR assay: In order to determine the degree of lynx1 expression, mRNA transcripts were quantitatively measured in mice. Mice were euthanized by CO2 asphyxiation according to animal welfare guidelines. Organs were harvested, homogenized and sonicated, and the RNA was extracted using RNAeasy Protect Mini kit (Qiagen) and treated with DNase (Qiagen). The RNA concentration was determined. RNA was diluted to 5 ng/ul and 50 ng of RNA was reverse transcribed with qScript cDNA Supermix (Quanta Bio). The qPCR was performed on 1 ng of cDNA per well, using assays from Life Technologies and PerfeCTa Fastmix II from Quanta Bio. Three replicates were performed per sample, and three animals were used. CT (cycle threshold) values of lynx1 were normalized against those of GAPDH levels. The data are represented as a percentage of brain expression, with 100% as the level of brain expression.

Figure 3:
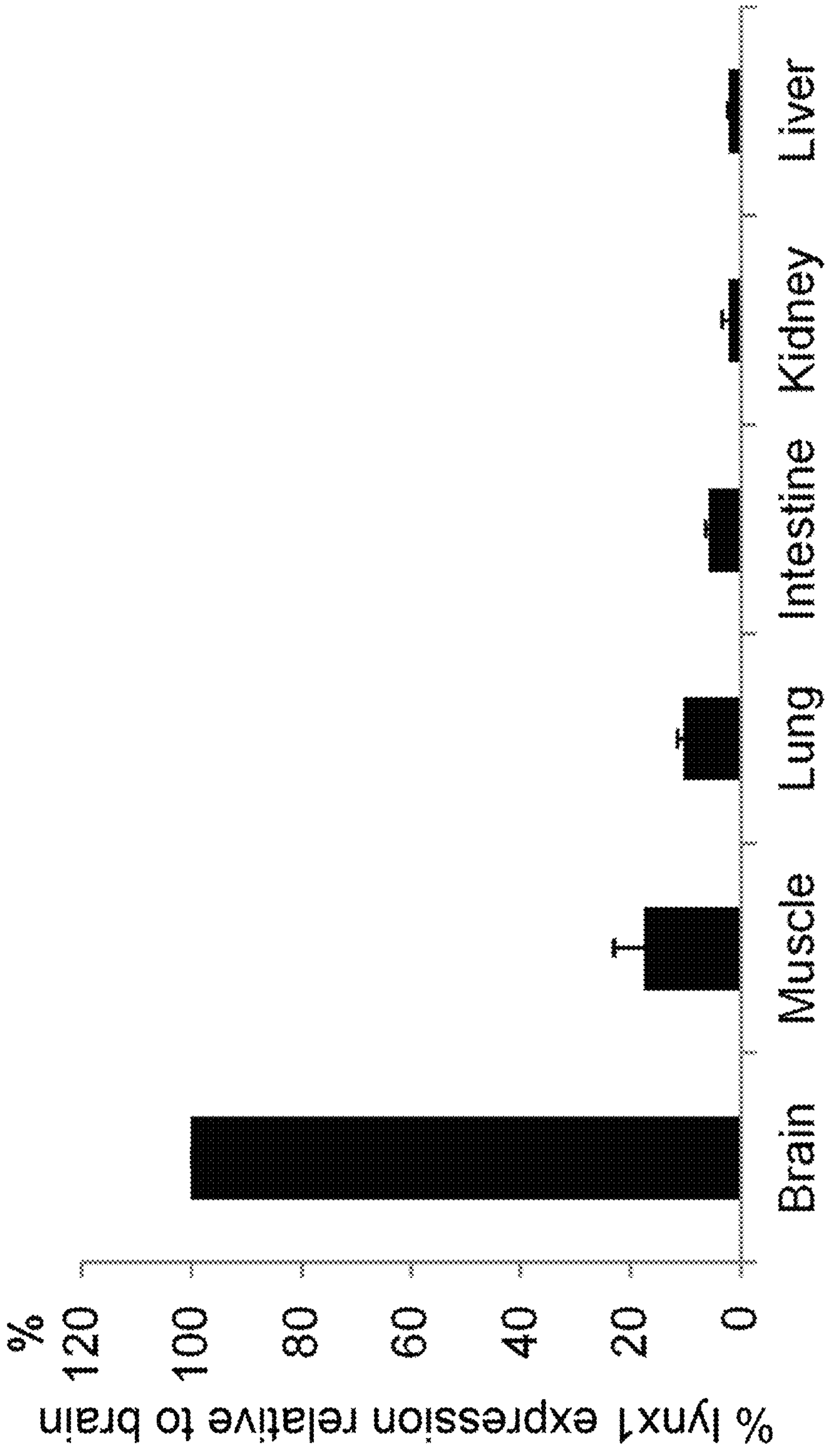
FIG. 3 is as graph comparing the lynx1 mRNA levels in tissue extracts from the brain, muscle, lung, intestine, kidney and liver relative to the amount of mRNA levels in the brain from a wild-type mouse, according to embodiments of the present invention.

Applied Biosystems's StepOne qPCR machine was used and TaqMan assays were developed for lynx1 and the nicotinic acetylcholine receptor subunits α4, α7, and β2. Lynx1 mRNA levels were measured in numerous tissues in the mouse (FIG. 3), cultured cortical neurons, and lynx1 stable cell lines. As shown in FIG. 3, the y-axis is the relative amount as a percentage of the brain expression levels, which were considerably higher than all other tissues. Intestine is the small intestine. Liver did not show lynx1 expression above background, and the kidneys had minimal lynx1 expression.

Example 3. α4β2 nAChR cell line transfected with lynx1. Transient versions of mouse nicotinic acetylcholine receptor subunits α4-yellow fluorescent protein (α4YFP) and β2-cyan fluorescent protein (β2CFP) show robust acetylcholine (ACh) and nicotine responses confirming the utility of using fluorescently tagged versions of α4 and β2 to isolate high quality cell lines. Following Nashmi et al. (*J of Neuroscience,* 2003, 23:11554-11567, 2003, the entire contents of which are incorporated herein by reference), α4 nicotinic acetylcholine receptor (nAChR) cDNAs were fused in frame with YFP, and β2 nAChRs were fused in frame with CFP, as described. Constructs were transfected into HEK293 cells, and treated with antibiotic to select for colonies with stable integration. Over 200 isolated selected clones underwent an iterative grading and culling process using analysis such as CFP and YFP fluorescent measurements, fluorescence resonance energy transfer (FRET) analyses (over 25% FRET efficiency), and functional analyses in the FlexStation® (a real-time fluorescence based multiwell plate reader with fluidics to measure nicotine responses). After these analyses, optimized α4YFPβ2CFP nAChR cell lines were further characterized using Western blot studies to detect protein levels of the receptors, and co-immunoprecipitation studies, to confirm the interaction of α4 with β2. After the α4YFPβ2CFP cell lines were selected and characterized, the best performing α4YFPβ2CFP stable cell line was transfected with a CMV (cytomegalovirus)-lynx1 construct. The clones from that transfection were selected again for stable integration of lynx1 from the parent α4YFPβ2CFP cell line. Over 20 colonies were selected, expanded and characterized. The parameters measured were FlexStation® measurements of the maximal nicotine induced response, and the dose-response to a serial dilution of nicotine. The best cell lines were expanded further and characterized by Western blot to determine the amount of lynx1 protein. In addition, the cell lines were subjected to co-immunoprecipitation studies in which the receptors were precipitated by anti-GFP antibodies, and the lynx protein was detected with anti-lynx1 antibodies to confirm the lynx1:receptor interaction. The functional difference of lynx1 to the receptors was further confirmed by patch-clamp electrophysiological measurements using pressure ejected nicotine pulses.

Figure 4A:
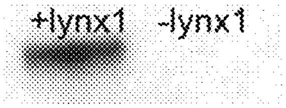
FIG. 4A is a Western blot of cell extracts from α4β2 nicotinic acetylcholine receptor cell lines that either express lynx1 (+lynx1) or do not express lynx1 (−lynx1), according to embodiments of the present invention.
Figure 4B:
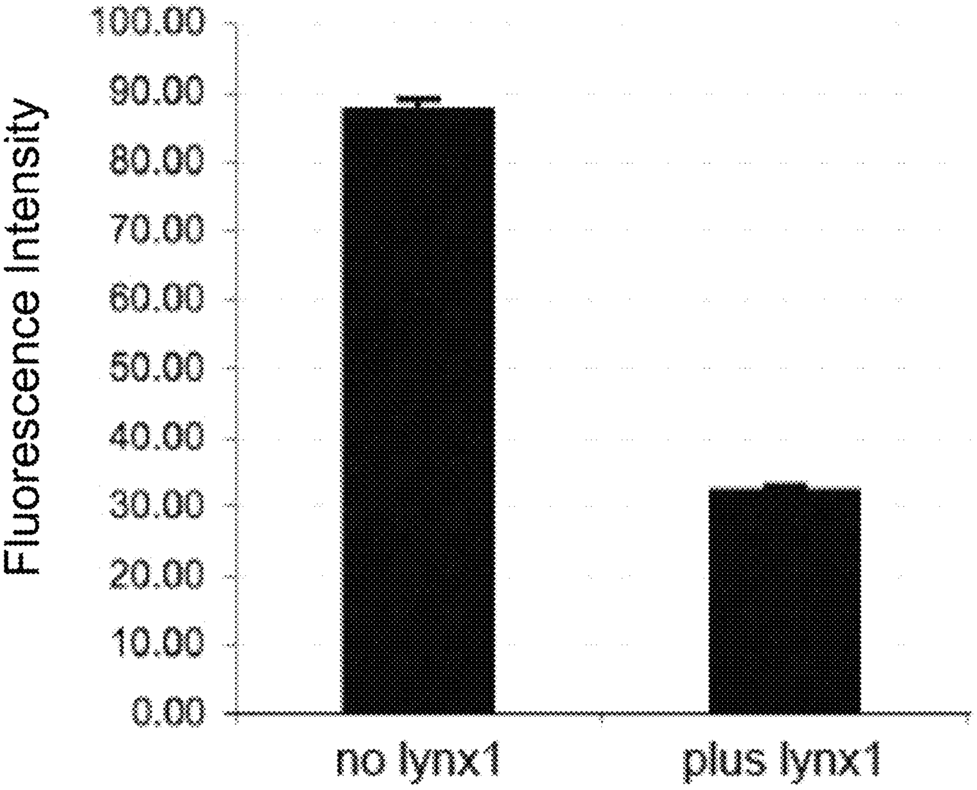
FIG. 4B is graph comparing the fluorescence intensity obtained from exposing nicotine to α4β2 nicotinic acetylcholine receptor cells lines that either express lynx1 (plus lynx1), or do not express lynx1 (no lynx1), using a fluorescent membrane potential dye to monitor physiological changes due to nicotinic acetylcholine receptor activity, according to embodiments of the present invention.

Measurable reduction of lynx1 in lynx1-α4YFPβ2CFP nAChR cell lines by Western blot analyses using commercially available anti-lynx1 monoclonal antibody, is shown in FIG. 4A. No lynx1 is detectable in −lynx1 cell lines, but is appreciably detected in +lynx cell lines. FlexStation® fluorescence is quantified in both the lynx1-α4YFPβ2CFP nAChR cell lines and the α4YFPβ2CFP nAChR cell lines (FIG. 4B). Using the difference in the maximal recordable signals in lynx1-α4YFPβ2CFP (plus lynx1) was compared to α4YFPβ2CFP nAChR cell lines which do not express lynx1 (no lynx1).

Maximal signal detectable with FlexStation® assay. Using a fluorescent dye responding to membrane potential, the FlexStation® plate reader measures the maximal signal obtained from exposing α4YFPβ2CFP nicotinic acetylcholine receptor cell lines either containing no lynx1 (left) or do contain lynx1 (right) to 100 μM of nicotine. Since nicotinic acetylcholine receptors are ion channels, binding of nicotine will result in a current across the cell membrane and a concomitant change in membrane potential. Any reduction of lynx1 expression within the lynx1 cell lines due to siRNA induced lynx1 mRNA degradation will increase the maximal signal up to the one seen for α4YFPβ2CFP cell lines alone.

Figure 5A:
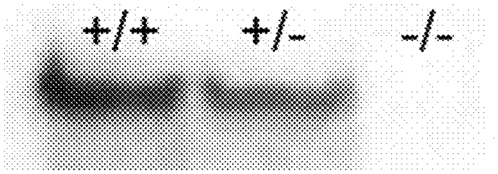
FIG. 5A is a Western blot of lynx1 protein in brain extracts from +/+(wild-type), +/− (lynx1 heterozygous knockout), and −/− (lynx1 homozygous knockout) mice using a polyclonal anti-lynx1 antibody, according to embodiments of the present invention.
Figure 5B:
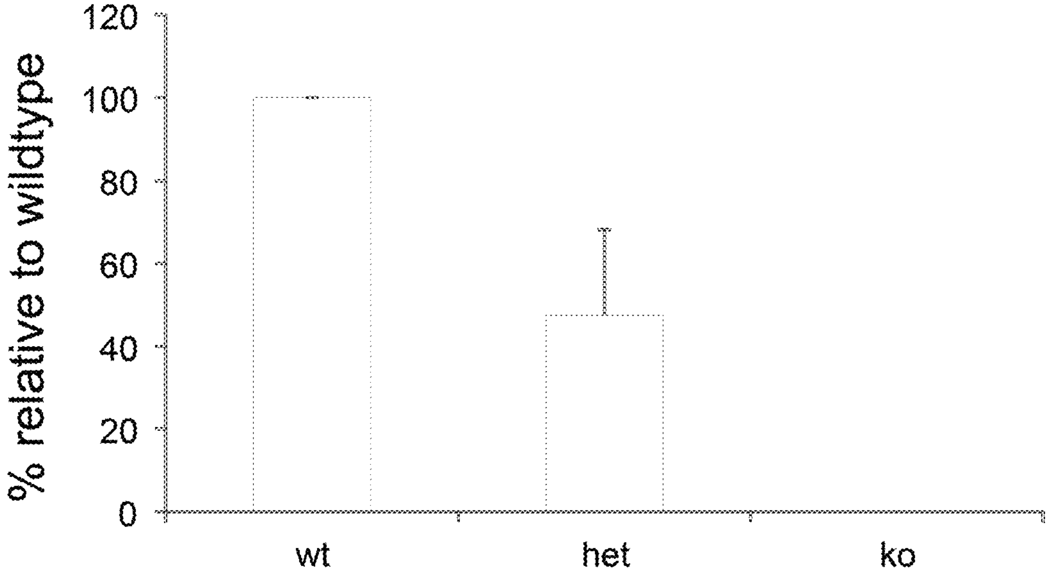
FIG. 5B is a graph comparing the normalized amounts of lynx1 protein levels as a percentage of wild-type cells, corresponding to the Western blot of FIG. 5A for WT, HET, and KO cells, according to embodiments of the present invention.

Example 4. Quantitative Western Blot assay: To monitor brain protein levels of lynx1, a quantitative Western Blot assay was established. Using a lynx1 antibody (purchased from Santa Cruz Biotechnology, Inc.) and a Li-Cor Odyssey machine, protein expression was quantified in wild-type, heterozygous and homozygous lynx1 KO mice (FIGS. 5A and 5B). Protein was extracted from brain tissue of lynx1KO mice (wild-type=+/+, heterozygous=+/−, and homozygous=−/−), lanes 1-3. Protein was blotted and detected using anti-lynx1 antibodies. Western blots were quantified (FIG. 5B) using a Li-Cor Odyssey detection system and normalized against the wild-type levels. The Y-axis shows a percentage of lynx1 levels compared to wild-type mice. The values are an average of four samples from four mice per genotype.

Figure 6:
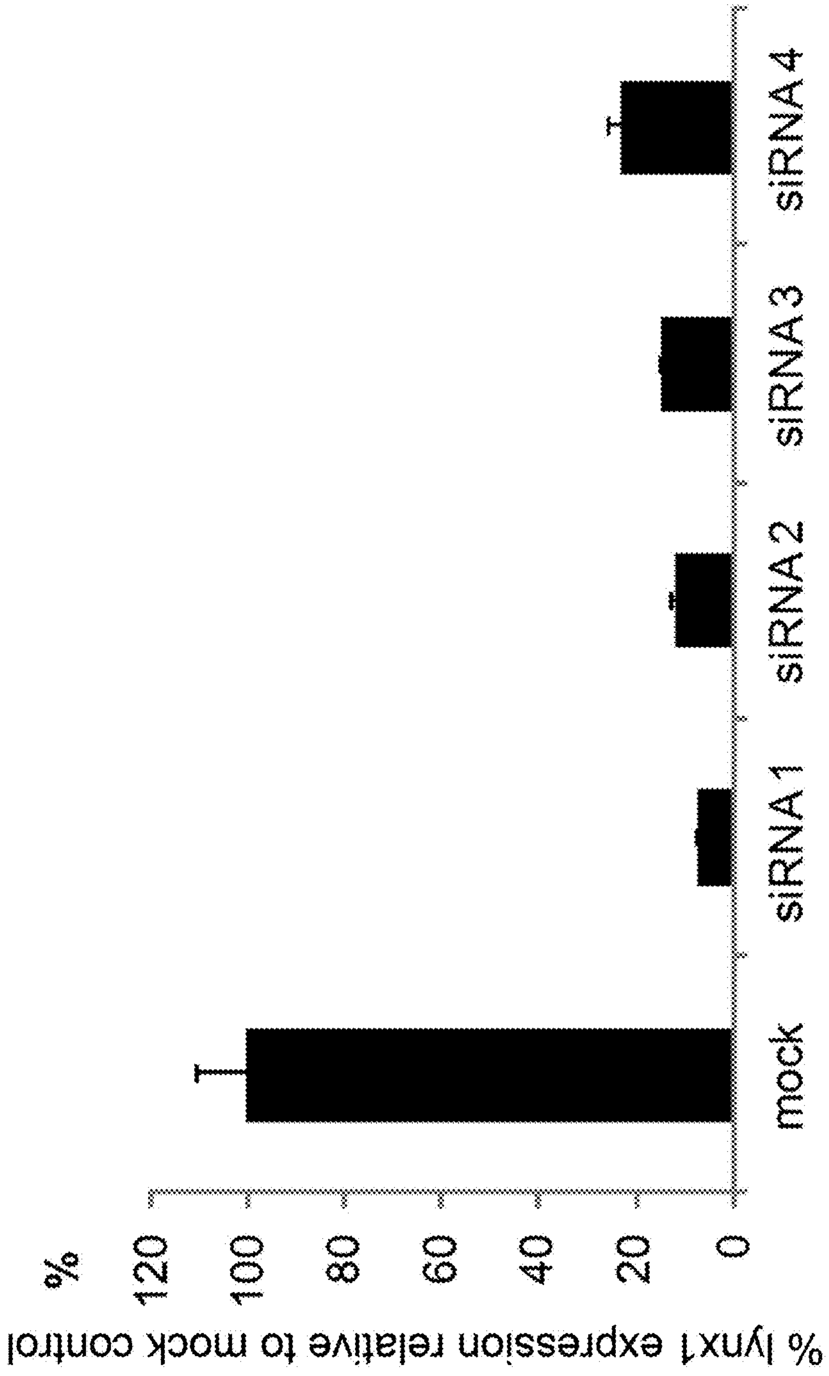
FIG. 6 is a graph comparing the lynx1 mRNA levels in neuronal cultures transfected with one of four different lynx1-siRNA species (siRNA1, siRNA2, siRNA3, or siRNA4) relative to a negative control transfection (mock), according to embodiments of the present invention.

Example 5. lynx1 knock-down in cells: Using the lynx1 TaqMan assays, lynx1 siRNA species were assayed for lynx1 knock-down in cultured cortical neurons (FIG. 6). Four siRNA species were purchased from Thermo Scientific/Dharmacon. Accell siRNA species were ordered, as follows: siRNA1 (GCACUGAUUUGAUAGAAUU) (SEQ ID NO:16), SMART pool siRNA A-062811-13 LYNX1; siRNA2: (CUUUGGUGCAUGGUUACUU) (SEQ ID NO:17), Accell SMART pool siRNA A-062811-14 LYNX1; siRNA 3: (GCAUCUGGGAGAAUGUUUA) (SEQ ID NO:18), Accell SMART pool siRNA A-062811-15 LYNX1; and siRNA4: (UGGUUAUCUAGAGUUGCAA) (SEQ ID NO:19), Accell SMART pool siRNA A-062811-16 LYNX1.

As shown in FIG. 6 lynx1 mRNA levels were measured in cortical neurons (mock) indicated an appreciable level of lynx1 expression in cultured neurons. For knock-down experiments, siRNAs were transfected into cultured neurons using the Accell method by Dharmacon (ThermoScientific). Each of siRNA1, siRNA2, siRNA3, and siRNA4 was used by itself or in combinations of 2, 3 or all 4. While all siRNAs and their combinations readily reduced the mRNA levels of lynx1, siRNA1 reduced lynx1 expression by more than 90%, as shown in FIG. 6. Accordingly, siRNA1 (GCACUGAUUUGAUAGAAUU) (SEQ ID NO:16), was subsequently used in complex with various peptides to assay neuronal uptake and transport in the brain.

Figure 7A:
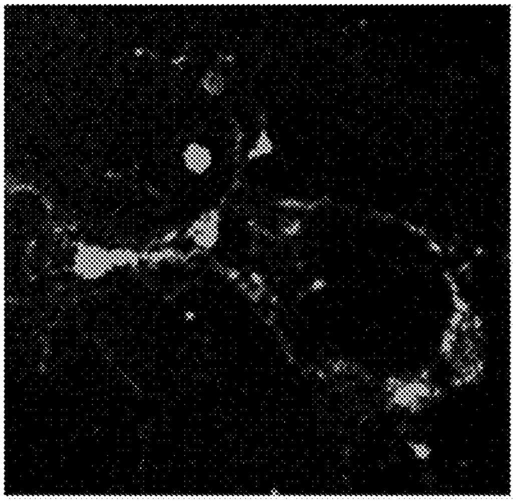
FIGS. 7A, 7B, 7C, and 7D are fluorescent images using fluorescent streptavidin detection of biotinylated lynx1-loop2 peptide (FIG. 7A); biotinylated RVG29 peptide (positive control) (FIG. 7B); biotinylated Ly6H-loop2 peptide (negative control) (FIG. 7C); and biotinylated lynx2-loop2 peptide (FIG. 7D) in primary neuronal cultures, according to embodiments of the present invention.

Example 6. Binding studies: The ability of the lynx1-loop2 peptide (SEQ ID NO:2) to bind to neurons in culture was determined. To carry this out, primary cortical neurons were cultured and the cultures were allowed to mature to the point at which they express nicotinic acetylcholine receptors. Cells were then bound with the indicated biotinylated peptide, which was then bound by fluorescent streptavidin, and the neurons were imaged using confocal microscopy. Neurons labeled on neurite-like processes using both RVG29 peptide YTIWMPENPRPGTPCDIFTNSRGKRASNG (SEQ ID NO:11) (Kumar et al., *Nature,* 448:39-43, 2007, the entire contents of which are incorporated herein by reference)(FIG. 7B) and lynx1-loop2 peptides (FIG. 7A). Additionally, equivalent numbers of neurons between RVG29 and lynx1-loop2 were observed in this assay, while the structurally similar ly6H-loop2 peptide (VRITDPSSSRKDHSVN) (SEQ ID NO:20), which is known not to bind nicotinic acetylcholine receptors (FIG. 7C) did not bind to neurons and the lynx2-loop2 peptide (EVMEQSAGIMYRKS)(SEQ ID NO:21) (FIG. 7D) did not reliably bind to neurons. As such, RVG29 is a positive control for lynx1-loop2 peptide and both ly6H-loop2 and lynx2-loop2 are negative controls.

Example 7. siRNA uptake studies of peptide-siRNA complexes into neurons. Experiments were carried out to assay lynx1-loop2 peptide-lynx1 siRNA complex in neurons and determine the degree of lynx1 knock-down and cellular uptake efficiency of this complex. Various complexes of peptide coupled with lynx1 siRNA (SEQ ID NO:16) (siRNA1) were incubated with primary neuronal cultures made from cortical mouse neurons. Unless indicated otherwise, lynx1 mRNA knock-down experiments were carried out as follows. The molar ratio of peptide to siRNA was 10:1. The final concentration of peptide and siRNA was 25 uM peptide (LifeTein)+2.5 uM lynx1 siRNA (Dharmacon). Peptides were complexed with siRNA for 30 minutes at room temperature in Neural Basal Media in half the final volume via a poly-D arginine linker attached to the C-terminal of the respective peptide. Complexes formed due to electrostatic (non-covalent) interactions between the positive charges of the arginines and the negative charges of the phosphate groups present in the siRNAs. After 30 minutes, half the final volume of Neural Basal Media (Invitrogen) containing 2× final concentration of the supplements B27 (Invitrogen) and GlutaMax (Invitrogen) was added. Complexes were vortexed thoroughly and added to the cells. Neuronal cultures were harvested after 24 hours of incubation, homogenized, and the RNA was extracted using RNAeasy Protect Mini kit (Qiagen) and treated with DNase (Qiagen). The RNA concentration was determined via Qubit (Life Technologies). RNA was diluted to 5 ng/ul and 50 ng of RNA was reverse transcribed with qScript cDNA Supermix (Quanta Bio). The qPCR was performed on 1 ng of cDNA per well, using assays from Life Technologies and PerfeCTa Fastmix II from Quanta Bio. Four replicates were performed per sample, and three samples were treated per condition. RQ values were calculated based on the CT values of lynx1, that was normalized against those of GAPDH levels (RQ=2^-deltadeltaCt). The data are represented as a percentage of knock-down, with 100% as the level of knock-down from the lynx1 loop2-lynx1 siRNA sample. Treatments with no level of mRNA reduction are represented as 0% knock-down. Samples were analyzed by student T-test.

Figure 8:
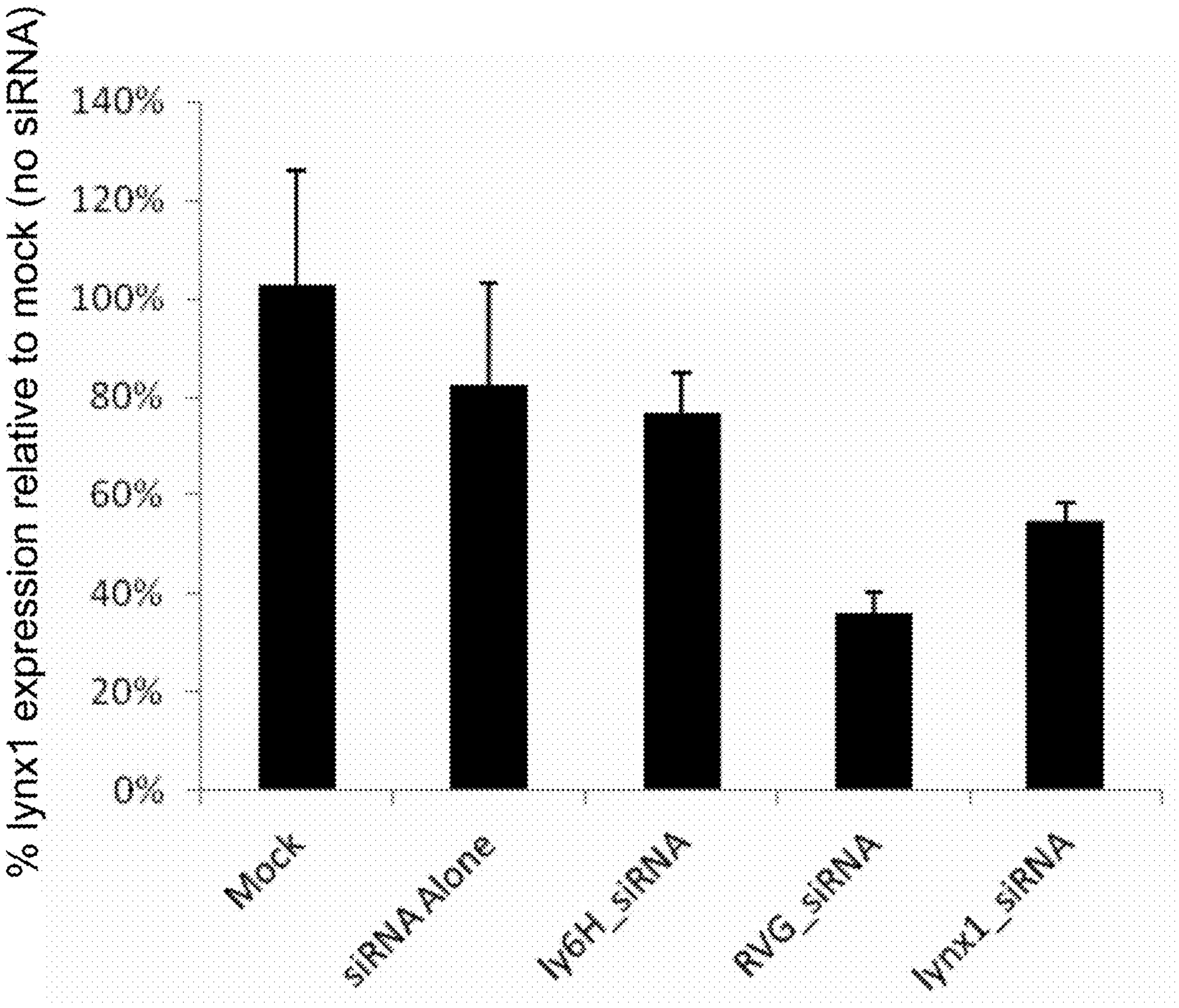
FIG. 8 is a graph showing the efficacy of a lynx1-loop2-linked lynx1 siRNA to knock down the expression of lynx1 in cultured neurons compared to no addition (Mock), lynx1 siRNA alone, ly6H-loop2 linked lynx1-siRNA, RVG29 linked lynx1-siRNA, and lynx1-loop2 linked lynx1-siRNA as indicated from left to right, according to embodiments of the present invention.

A reduction in lynx1 mRNA was observed when the lynx1 siRNA molecules were complexed with lynx1-loop2 peptide or when complexed with RVG29 peptide, compared to no siRNA (Mock). The negative control peptide, ly6H-loop2, and naked siRNA (siRNA Alone) showed no significant reduction in lynx1 mRNA levels (FIG. 8). These data demonstrate the ability of lynx1-loop 2 peptide to carry siRNA molecules into neurons.

Example 8. Knock-down of lynx1 mRNA after delivery of anti-lynx1 siRNA into cultured cortical neurons via peptide-siRNA complexes. To test the ability of different lynx1-loop2 peptide variants to deliver siRNA into cultured cortical neurons, several different complexes of peptide variants with anti-lynx1 siRNA were prepared. These complexes were added to neuronal cultures and the ability of the peptide to translocate the siRNA into the neurons was measured by qPCR. The results are shown in FIG. 10. Four lynx1-loop2 variants were assayed. These variants are referred to as Mutant 1 (MTWCDYFTPSRGKVRKS) (SEQ ID NO:4), Mutant 2 (MTTRTYATPYRMKVRKS) (SEQ ID NO:6), Mutant 3 (MTTRTYFTPYAMADRKS)(SEQ ID NO:7) and Mutant 4

```
(MTTMPENPRPGTPRTYFTPYRMKVRKS      (SEQ ID NO: 10)
```

which were compared against lynx1-loop2 peptide (SEQ ID NO:2). Negative controls are Ly6H-loop2 peptide (SEQ ID NO:20), uncomplexed siRNA (no peptide), and a mock incubated samples. RVG29 peptide (SEQ ID NO:11) and RVG19 peptide YTIWCDIFTNSRGKRASNG (SEQ ID NO:12) were both conjugated to lynx1-siRNA and assayed for comparison. The level of knock-down of lynx1 mRNA levels is presented as a percentage of the lynx1-loop2 peptide-siRNA complex.

Primary cortical cultures were prepared from wild-type mice, and cultures were incubated for approximately 2 weeks in a 48-well dish. Neurons were incubated with a complex of 5 μM peptide and 0.5 μM siRNA (a 10:1 molar ratio) for 24 hours. Complexes formed via a poly-D arginine linker attached to the C-terminal of the respective peptide. Cells were harvested and mRNA isolated, transcribed into cDNA and analyzed using qPCR. Data is displayed as a comparison between lynx1-loop2 peptide efficiency (100%) with the indicated peptides. Therefore, lower percentage indicates less effective delivery of siRNA into cultured neurons. siRNA alone (no peptide) is set at 0%.

TABLE 1

Lynx1-loop2 variants (SEQ ID NOS 2, 3, 2, 24, 2 and 5, respectively, in order of appearance).

| amino acid position | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| lynx1-loop2 variant 1 | M | T | T | R | T | Y | **F** | T | P | **Y** | R | M | K | V | **R** | K |
| lynx1-loop2 variant 2 | - | - | - | - | - | - | **Y** | - | - | **T** | - | - | - | - | **S** | - |
| Block 1 of amino acids | - | - | **T** | **R** | **T** | - | **F** | - | - | - | - | - | - | - | - | - |
| variant | - | - | **W** | **C** | **D** | - | **F** | - | - | - | - | - | - | - | - | - |
| Block 2 of amino acids | - | - | - | - | - | - | - | - | - | - | **R** | **M** | **K** | **V** | - | - |
| variant | - | - | - | - | - | - | - | - | - | - | **R** | **G** | **K** | **V** | - | - |

Mutant 1 contains the alternate variants of both the first and second block of amino acids described in Table 1 above (i.e. WCD instead of lynx1 TRT and RGKV (SEQ ID NO: 25) instead of lynx1 RMKV (SEQ ID NO: 22)). This Mutant 1 (with SEQ ID NO:4 peptide) is as capable of translocating siRNA into neurons as is lynx1-loop2 indicating that both blocks are functional in either variety. Mutant 2 (with SEQ ID NO:6 peptide) replaces the F of the first block with an A and this substitution significantly reduces lynx1-loop2 peptide ability to transport siRNA into neurons and subsequent knock-down indicating the utility of the phenylalanine (F) at this position. Mutant 3 (with SEQ ID NO:7 peptide) replaces the R (arginine), the K (lysine), and the V (valine) in the R(M/G)KV motif with A (alanine), A (alanine), and D (aspartic acid), respectively. Mutant 4 (with SEQ ID NO:10) is a variant of SEQ ID NO; 2 with MPENPRPGTP (SEQ ID NO:8) inserted between residues 3 and 4. As shown, the substitutions of Mutant 3 abolish lynx1-loop2 peptide function, indicating the utility of these amino acids in this block. Ly6H-loop2, siRNA alone, and mock treatment did not result in knock-down of lynx1 mRNA, and Mutant 1 and Mutant 4 enhanced the knock-down compared to SEQ ID NO:2 peptide. Interestingly, SEQ ID NO:2 (lynx1-loop2), Mutant 1 and Mutant 4 were more effective at decreasing levels of lynx1 mRNA compared to RVG29 and RVG19.

Example 9. Delivery of peptide-complexes into capillary endothelial cells in mouse brain. To identify whether lynx1-loop2 peptides can transport siRNA into the brain, fluorescently labeled siRNA was visualized in brain sections of intravenously injected mice. Lynx1-loop2 was conjugated in a complex with a specifically modified siRNA that is capable of being fluorescently visualized and located within the nucleus of a cell (siGLO from Thermo Scientific/Dharmacon), following manufacturer's instructions. RVG29 peptide (SEQ ID NO:11)-siRNA complex is the positive control and ly6H-loop2 (SEQ ID NO:20)-siRNA complex is the negative control.

Lynx1-loop2 peptide (SEQ ID NO:2) conjugated to nuclear siRNA was injected into the tail vein and the animal was sacrificed 2 hours later. Fluorescently labeled nuclei were identified in what appears to be brain capillary endothelial cells. It was reasoned that 2 hours was enough time for peptide-siRNA uptake into epithelial cells, but not enough time to have the peptide-siRNA complex traverse the blood vessels into the actual brain. As such, this constitutes the first step of blood-brain barrier crossing. Similar staining could be seen in RVG29-siRNA complex injected mice, but no such staining was seen in ly6H-loop2-siRNA complex injected mice.

Complexes were prepared by mixing peptide molecules with fluorescently conjugated siRNA molecules designed to enter the cell nucleus at a 10:1 molar ratio. Specifically, peptides were purchased from LifeTein and complexed with siGLO siRNA (Dharmacon) at a final concentration of 38.7 uM peptide and 3.87 uM siGLO for 30 minutes at room temperature. Samples were vortexed thoroughly and animals were dosed at 50 ml/kg. CD-1 mice, weighing no more than 33 grams were injected through the tail vein and perfused transcardially 2 hours later with 4% paraformaldehyde. Brains were post-fixed for 2 hours in 4% paraformaldehyde on ice and sunk in 30% sucrose containing 1% paraformaldehyde overnight at 4 degrees Celsius. The brains were sectioned at 30 microns. After mounting sections on microscope slides, fluorescent siRNA molecules were detected through confocal microscopy. The identity of blood vessels was confirmed by bright field imaging.

Figures 11A, 11B, 11C, 11D:
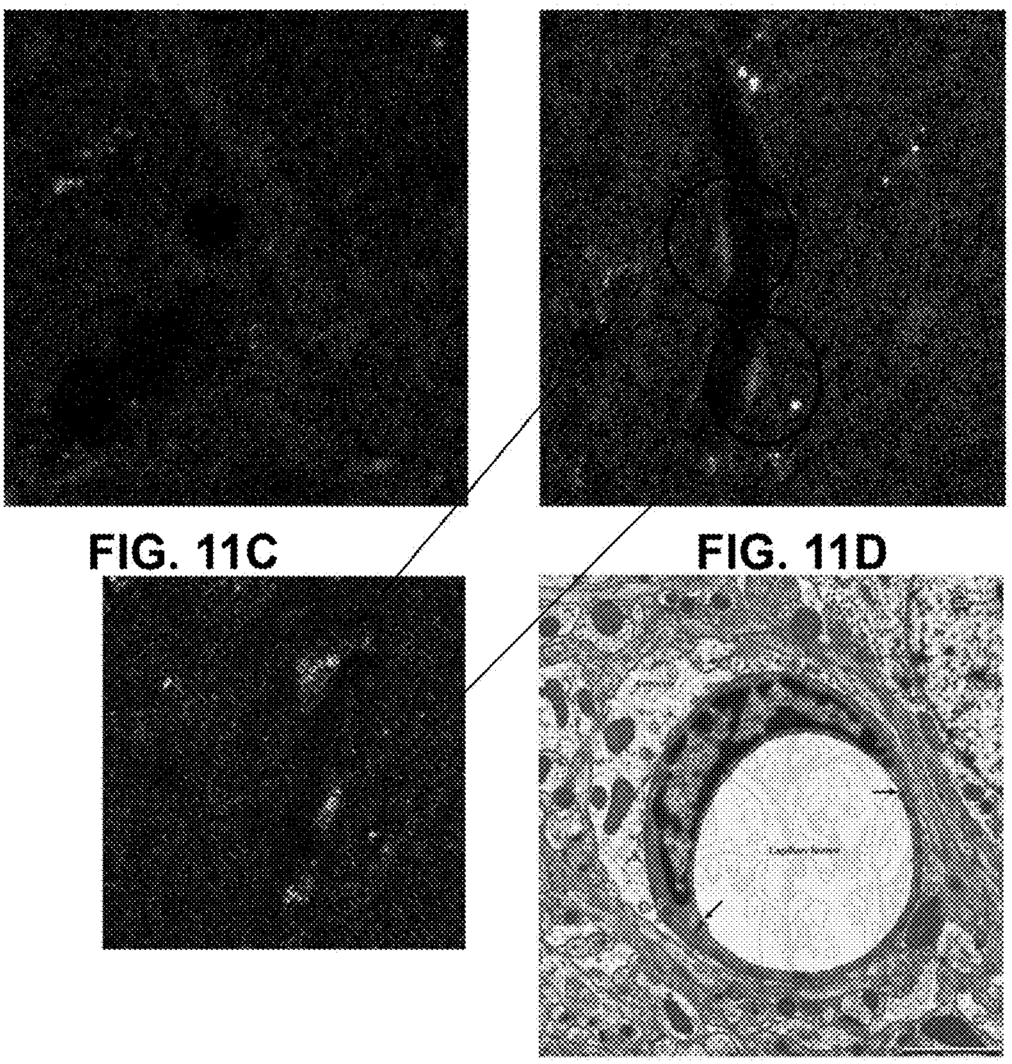
FIG. 11A is a confocal microscopy image of brain sections from a mouse injected with a fluorescently labeled nuclear siRNA conjugated with ly6H-loop2 peptide (negative control), according to embodiments of the present invention.
FIG. 11B is a confocal microscopy image of brain sections from a mouse injected with a fluorescently labeled nuclear siRNA conjugated with lynx1-loop2 peptide with circles around the concentrated fluorescence, according to embodiments of the present invention.
FIG. 11C is an optical zoom of the circled fluorescence in FIG. 11B, in which the labeled cells display the sickle shape characteristic of capillary endothelial cells, according to embodiments of the present invention.
FIG. 11D is a representative electron microscopic image of a cross-section of a capillary endothelial cell surrounding the lumen of a capillary.

FIGS. 11A, 11B, and 11C show images of nuclear fluorescently labeled siRNA after translocation into brain capillary endothelial cells. FIG. 11A is a confocal microscopy image of brain sections from a negative control animal (injected with ly6H-loop2 control peptide-conjugated with fluorescent siGLO) which does not show staining of blood vessels. FIG. 11B is a confocal microscopy image from brain sections of mice injected with a complex derived from lynx1-loop2 peptide conjugated with fluorescently labeled nuclear siRNA. The images depict a blood capillary displaying uptake of peptide-siRNA complex within capillary endothelial cells. Fluorescence is sickle shaped, reflecting the morphology of the capillary endothelial cell as shown in the reference electron microscopic (EM) image of FIG. 11D. FIG. 11C is an optical zoom of image FIG. 11B, showing two labeled cells (white arrows) displaying the sickle shape, at the edge of the lumen of the capillary. FIG. 11D is a representative electron microscope (EM) image in cross-section of a capillary endothelial cell surrounding the lumen of a capillary. The morphology displays a long, thin, crescent shape, the sickle morphology at the border of the lumen of the blood capillary similar to the shapes seen in FIGS. 11B and 11C.

Figure 7B:
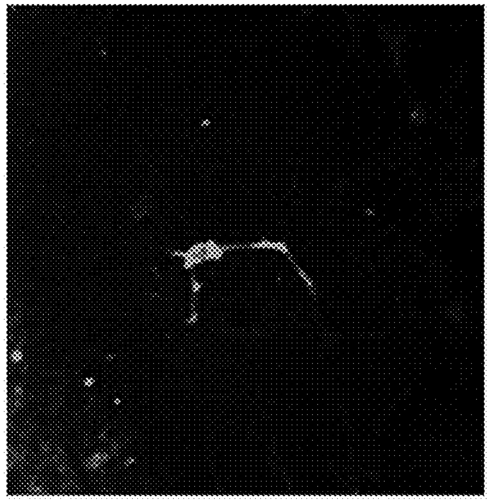
Figure 7C:
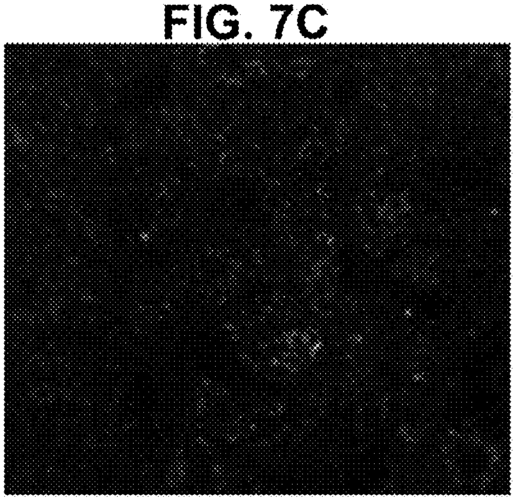
Figure 7D:
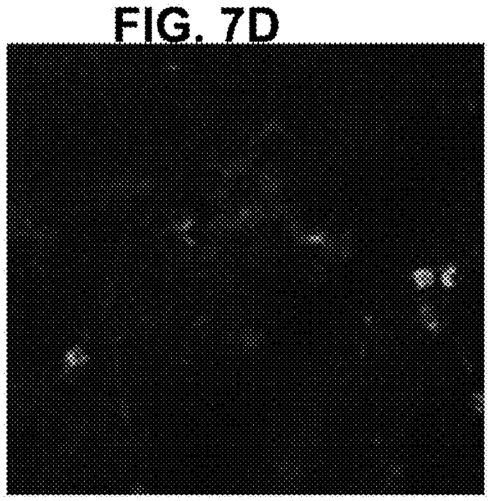

As disclosed throughout and evidenced by the figures, a lynx1-loop2-derived peptide is capable of crossing the blood brain barrier. For example, as shown in FIG. 7B, lynx1-loop2 peptide is taken up in primary neuronal cultures. Additionally, the mRNA knockdown data of FIG. 10 and the confocal microscopy of FIGS. 11A-11C show that lynx1-loop2-derived peptides are capable of delivering an effector agent across the blood brain barrier and into neurons. Furthermore, methods are provided for using a lynx1-loop2-derived peptide alone and in complex with at least an effector agent for crossing the blood brain barrier.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A peptide consisting of $X_1$-$X_2$-$X_3$-$X_4$-$X_5$-$X_6$-$X_7$-$X_8$-$X_9$-$X_{10}$-R-$X_{12}$-K-$X_{14}$-$X_{15}$-$X_{16}$, (SEQ ID NO:1) in which $X_1$ is M or T;

$X_2$ is T or I;

$X_3$ is T or W;

$X_4$ is R or C;

$X_5$ is T or D;

$X_6$ is Y, I, or G;

$X_7$ is F or Y;

$X_8$ is T or C;

$X_9$ is P, N, or S;

$X_{10}$ is Y, T, or S;

$X_{12}$ is M or G;

$X_{14}$ is V or R;

$X_{15}$ is R, S, A, or I; and $X_{16}$ is K, S, or D or SEQ ID NO: 1 optionally including up to 5 amino acid additions and optionally conjugated to an effector agent, the peptide being capable of transport across the blood brain barrier.

2. The peptide of claim 1, wherein the peptide consists of SEQ ID NO: 4, SEQ ID NO: 6 or SEQ ID NO: 7 optionally including up to 5 amino acid additions and optionally conjugated to an effector agent.

3. The peptide of claim 1, wherein the up to 5 amino acid additions comprises one or more A, D or S residues.

4. A composition comprising a peptide consisting of SEQ ID NO:1 or SEQ ID NO:1 optionally including up to 5 amino acid additions; and an effector agent, wherein the effector agent is optionally conjugated to the peptide.

5. The composition of claim 4, wherein the effector agent is conjugated to the peptide.

6. The composition of claim 4, wherein the effector agent is selected from the group consisting of siRNA, shRNA, microRNA, double stranded RNA, strand template RNA, oligonucleotides, modified oligonucleotides, aptamers, analogs and combinations of oligonucleotides, genes, peptides, proteins, small chemical molecules, large chemical molecules, viral particles, liposomes, endosomes, exosomes, nanoparticles, dendrimers, positron emission tomography (PET) ligands, eukaryotic cells, prokaryotic cells, microspheres, nanogels, and bionanocapsules.

7. The composition of claim 4, wherein the effector agent is siRNA.

8. The composition of claim 4, wherein the effector agent is siRNA and is conjugated to the peptide.

9. The composition of claim 4, wherein the effector agent is conjugated to the peptide by a linker, chemical modification, peptide linker, chemical linker, covalent or non-covalent bond, or protein fusion.

10. The composition of claim 9, wherein the linker comprises a polyarginine linker.

11. A composition comprising a peptide consisting of SEQ ID NO:1 or SEQ ID NO:1 optionally including up to 5 amino acid additions, wherein the up to 5 amino acid additions comprises one or more A, D, or S residues; and an effector agent, wherein the effector agent is optionally conjugated to the peptide.

12. The composition of claim 11, wherein the effector agent is conjugated to the peptide.

13. The composition of claim 11, wherein the effector agent is selected from the group consisting of siRNA, shRNA, microRNA, double stranded RNA, strand template RNA, oligonucleotides, modified oligonucleotides, aptamers, analogs and combinations of oligonucleotides, genes, peptides, proteins, small chemical molecules, large chemical molecules, viral particles, liposomes, endosomes, exosomes, nanoparticles, dendrimers, positron emission tomography (PET) ligands, eukaryotic cells, prokaryotic cells, microspheres, nanogels, and bionanocapsules.

14. The composition of claim 11, wherein the effector agent is siRNA.

15. The composition of claim 11, wherein the effector agent is siRNA and is conjugated to the peptide.

16. The composition of claim 11, wherein the effector agent is conjugated to the peptide by a linker, chemical modification, peptide linker, chemical linker, covalent or non-covalent bond, or protein fusion.

17. The composition of claim 16, wherein the linker comprises a polyarginine linker.

18. A method of transporting a peptide to a target found within the blood brain barrier, the method comprising providing the peptide of claim 1 to the target, the target being in vivo or in vitro.

19. A method of transporting a peptide to a target found within the blood brain barrier, the method comprising providing the peptide of claim 3 to the target, the target being in vivo or in vitro.

* * * * *